(12) United States Patent
Ciavarella

(10) Patent No.: US 11,000,161 B2
(45) Date of Patent: *May 11, 2021

(54) HIGH QUALITY NON-AEROSOL HAND SANITIZING FOAM

(71) Applicant: GOJO Industries, Inc., Akron, OH (US)

(72) Inventor: Nick E. Ciavarella, Seven Hills, OH (US)

(73) Assignee: GOJO Industries, Inc., Akron, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 16/600,699

(22) Filed: Oct. 14, 2019

(65) Prior Publication Data

US 2020/0037826 A1 Feb. 6, 2020

Related U.S. Application Data

(63) Continuation of application No. 15/429,389, filed on Feb. 10, 2017, now Pat. No. 10,441,115, which is a
(Continued)

(51) Int. Cl.
*A47K 5/14* (2006.01)
*F04B 43/04* (2006.01)
(Continued)

(52) U.S. Cl.
CPC ............... *A47K 5/14* (2013.01); *A61K 9/122* (2013.01); *A61K 31/045* (2013.01);
(Continued)

(58) Field of Classification Search
CPC ......... A47K 5/14; F04B 45/043; F04B 23/06; F04B 13/02; F04B 23/02; F04B 19/06;
(Continued)

(56) References Cited

U.S. PATENT DOCUMENTS 3,937,364 A  2/1976 Wright
3,970,219 A  7/1976 Spitzer
(Continued)

FOREIGN PATENT DOCUMENTS

CN  202370781 U  8/2012
CN  202493407 U  10/2012
(Continued)

OTHER PUBLICATIONS

Notice of Allowance for U.S. Appl. No. 15/355,112 dated May 21, 2018.
(Continued)

*Primary Examiner* — Patrick M. Buechner
(74) *Attorney, Agent, or Firm* — Calfee, Halter & Griswold LLP

(57) ABSTRACT

Exemplary embodiments of high non-aerosol foam sanitizers are disclosed herein. An exemplary embodiment of high non-aerosol foam sanitizer includes a liquid mixture that includes an alcohol, water and a surfactant mixed with and entrapping air to form a plurality of foam bubbles. Wherein more than about 50 percent of the foam bubbles have a size of between about 50 m and about 250 μm.

20 Claims, 16 Drawing Sheets

US 11,000,161 B2

Page 2

Related U.S. Application Data continuation-in-part of application No. 15/369,007, filed on Dec. 5, 2016, now Pat. No. 10,080,468, and a continuation-in-part of application No. 15/355,112, filed on Nov. 18, 2016, now Pat. No. 10,080,466, and a continuation-in-part of application No. 15/356,795, filed on Nov. 21, 2016, now Pat. No. 10,080,467, and a continuation-in-part of application No. 15/350,190, filed on Nov. 14, 2016, now Pat. No. 10,065,199.

(60) Provisional application No. 62/293,931, filed on Feb. 11, 2016, provisional application No. 62/319,061, filed on Apr. 6, 2016.

(51) Int. Cl.
  *B05B 7/04* (2006.01)
  *B05B 7/24* (2006.01)
  *A61K 9/12* (2006.01)
  *A61K 31/045* (2006.01)
  *F04B 45/04* (2006.01)
  *F04B 23/06* (2006.01)
  *F04B 13/02* (2006.01)
  *F04B 23/02* (2006.01)
  *F04B 19/06* (2006.01)
  *F04B 43/02* (2006.01)
  *F04B 49/06* (2006.01)
  *F04B 45/047* (2006.01)

(52) U.S. Cl.
  CPC .......... *B05B 7/0416* (2013.01); *B05B 7/2402* (2013.01); *F04B 13/02* (2013.01); *F04B 19/06* (2013.01); *F04B 23/02* (2013.01); *F04B 23/06* (2013.01); *F04B 43/026* (2013.01); *F04B 43/04* (2013.01); *F04B 45/043* (2013.01); *F04B 45/047* (2013.01); *F04B 49/06* (2013.01)

(58) Field of Classification Search
  CPC ...... F04B 43/04; F04B 43/025; F04B 43/026; F04B 43/02; F04B 49/06; F04B 45/047; F04B 45/04; B05B 7/0416; B05B 7/2402; A61K 9/122; A61K 31/045
  See application file for complete search history.

(56) References Cited

U.S. PATENT DOCUMENTS

| | | | |
|---|---|---|---|
| 4,022,351 A | 5/1977 | Wright | |
| 4,044,923 A | 8/1977 | Gardner | |
| 4,049,830 A | 9/1977 | Pugliese | |
| 4,184,615 A | 1/1980 | Wright | |
| 4,219,159 A | 8/1980 | Wesner | |
| 4,274,594 A | 6/1981 | Ito | |
| 4,371,517 A | 2/1983 | Vanlerberghe | |
| 4,678,668 A | 7/1987 | Darras | |
| 4,801,249 A | 1/1989 | Kakizawa | |
| 4,940,702 A | 7/1990 | Finch | |
| 4,945,110 A | 7/1990 | Brokken | |
| 5,028,407 A | 7/1991 | Finch | |
| 5,028,427 A * | 7/1991 | Finch | A61P 31/04 424/114 |
| 5,063,249 A | 11/1991 | Andrews | |
| 5,129,550 A | 7/1992 | Eschbach | |
| 5,208,257 A | 5/1993 | Kabara | |
| 5,370,815 A | 12/1994 | Kessler | |
| 5,529,770 A | 6/1996 | McKinzie | |
| 5,534,266 A | 7/1996 | Ricketts | |
| 5,575,993 A | 11/1996 | Ward | |
| 5,616,348 A | 4/1997 | Winicov | |
| 5,635,469 A | 6/1997 | Fowler | |
| 5,720,984 A | 2/1998 | Ricketts | |
| 5,791,882 A | 8/1998 | Stucker et al. | |
| 5,842,607 A | 12/1998 | Snider | |
| 5,843,912 A | 12/1998 | Hosmane | |
| 5,967,202 A | 10/1999 | Mullen | |
| 6,082,586 A | 7/2000 | Banks | |
| 6,264,438 B1 | 7/2001 | Fukami | |
| 6,302,058 B1 | 10/2001 | Dahl | |
| 6,382,928 B1 | 5/2002 | Chang | |
| 6,544,539 B1 | 4/2003 | Ricketts | |
| 6,871,679 B2 | 3/2005 | Last | |
| 7,040,876 B2 | 5/2006 | Fukami et al. | |
| 7,451,687 B2 | 11/2008 | Lynn | |
| 7,511,007 B2 * | 3/2009 | Tichy | A61Q 5/02 510/372 |
| 7,647,954 B2 | 1/2010 | Garber et al. | |
| 7,850,049 B2 | 12/2010 | Ciavarella et al. | |
| 7,887,304 B2 | 2/2011 | Cal | |
| 8,272,539 B2 | 9/2012 | Ophardt et al. | |
| 8,276,784 B2 | 10/2012 | Ciavarella | |
| 8,304,375 B1 | 11/2012 | Wolff | |
| 8,449,267 B2 | 5/2013 | Pascual | |
| 8,544,698 B2 | 10/2013 | Ciavarella et al. | |
| 8,734,132 B2 | 5/2014 | Brender A Brandis | |
| 8,763,863 B2 | 7/2014 | Quinlan et al. | |
| 8,820,585 B1 | 9/2014 | Banks | |
| 8,845,309 B2 | 9/2014 | Cal | |
| 8,955,718 B2 | 2/2015 | Ciavarella et al. | |
| 8,960,498 B2 | 2/2015 | Weglin et al. | |
| 9,341,176 B2 | 5/2016 | Itahara | |
| 9,596,963 B2 | 3/2017 | Harris et al. | |
| 10,065,199 B2 | 9/2018 | Twaroski | |
| 10,080,466 B2 | 9/2018 | Ciavarella | |
| 10,080,467 B2 | 9/2018 | Ciavarella | |
| 10,080,468 B2 | 9/2018 | Ciavarella | |
| 10,143,339 B2 | 12/2018 | Ciavarella | |
| 10,441,115 B2 | 10/2019 | Ciavarella | |
| 2002/0051717 A1 | 5/2002 | Fukami | |
| 2003/0031571 A1 | 2/2003 | Yamakawa | |
| 2003/0068234 A1 | 4/2003 | Shindo | |
| 2003/0068242 A1 | 4/2003 | Yamakawa | |
| 2004/0266649 A1 | 12/2004 | Thekkekandam | |
| 2005/0049513 A1 | 3/2005 | Hori | |
| 2005/0129626 A1 * | 6/2005 | Koivisto | A61L 2/235 424/47 |
| 2005/0258192 A1 | 11/2005 | Matthews | |
| 2006/0281663 A1 | 12/2006 | Asmus | |
| 2007/0148101 A1 | 6/2007 | Snyder | |
| 2007/0237901 A1 | 10/2007 | Moses | |
| 2008/0051314 A1 | 2/2008 | Wenzel | |
| 2009/0098067 A1 * | 4/2009 | Seidling | A61K 8/891 424/59 |
| 2009/0200340 A1 | 8/2009 | Ophardt | |
| 2009/0294478 A1 | 12/2009 | Ciavarella | |
| 2009/0317270 A1 | 12/2009 | Reynolds | |
| 2010/0051642 A1 | 3/2010 | Wong | |
| 2010/0102083 A1 | 4/2010 | Quinlan | |
| 2010/0143265 A1 * | 6/2010 | Hewes | A61P 31/00 424/43 |
| 2010/0270328 A1 | 10/2010 | Quinlan | |
| 2012/0285992 A1 | 11/2012 | Ciavarella et al. | |
| 2012/0309660 A1 | 12/2012 | Kawasoe | |
| 2012/0315166 A1 | 12/2012 | Looi et al. | |
| 2013/0017110 A1 | 1/2013 | Villagomez | |
| 2013/0032614 A1 | 2/2013 | Babikian | |
| 2013/0056497 A1 | 3/2013 | McNulty | |
| 2013/0165530 A1 | 6/2013 | Hillman | |
| 2013/0175296 A1 | 7/2013 | Gray | |
| 2013/0200098 A1 | 8/2013 | Li | |
| 2013/0206794 A1 | 8/2013 | McNulty et al. | |
| 2013/0233441 A1 | 9/2013 | Ciavarella | |
| 2013/0259818 A1 * | 10/2013 | Adamo | A61Q 5/02 424/70.13 |
| 2013/0287712 A1 * | 10/2013 | Wolff | A61P 31/00 424/59 |
| 2014/0034679 A1 * | 2/2014 | Fitzpatrick | A47K 5/14 222/190 |
| 2014/0054322 A1 | 2/2014 | McNulty et al. | |
| 2014/0054323 A1 | 2/2014 | McNulty et al. | |
| 2014/0061246 A1 | 3/2014 | McNulty et al. | |

(56) References Cited

U.S. PATENT DOCUMENTS

| | | | |
|---|---|---|---|
| 2014/0079648 A1* | 3/2014 | Cohen | A61P 31/02 424/45 |
| 2014/0117053 A1 | 5/2014 | Ciavarella | |
| 2014/0154117 A1 | 6/2014 | Fukami | |
| 2014/0189992 A1 | 7/2014 | Ganzeboom | |
| 2014/0203047 A1 | 7/2014 | McNulty | |
| 2014/0234140 A1 | 8/2014 | Curtis et al. | |
| 2014/0243417 A1 | 8/2014 | Modak | |
| 2014/0272106 A1 | 9/2014 | Copeland et al. | |
| 2014/0367419 A1 | 12/2014 | Harris et al. | |
| 2015/0025156 A1 | 1/2015 | Hillman | |
| 2015/0080478 A1 | 3/2015 | Cohen | |
| 2015/0090737 A1 | 4/2015 | Ciavarella | |
| 2015/0209811 A1 | 7/2015 | Ophardt et al. | |
| 2015/0251841 A1 | 9/2015 | McNulty et al. | |
| 2015/0266657 A1 | 9/2015 | Corney | |
| 2015/0297728 A1 | 10/2015 | Charboneau | |
| 2015/0320266 A1 | 11/2015 | Creaghan | |
| 2015/0337820 A1 | 11/2015 | Cai | |
| 2016/0029855 A1 | 2/2016 | Harris et al. | |
| 2016/0256016 A1 | 9/2016 | Yang | |
| 2017/0135531 A1 | 5/2017 | Mak | |
| 2017/0135532 A1 | 5/2017 | Ciavarella | |
| 2017/0136475 A1 | 5/2017 | Twaroski | |
| 2017/0143172 A1 | 5/2017 | Ciavarella | |
| 2017/0156550 A1 | 6/2017 | Ciavarella | |
| 2017/0231437 A1 | 8/2017 | Ciavarella | |
| 2017/0290470 A1 | 10/2017 | Ciavarella | |
| 2018/0235410 A1 | 8/2018 | Ciavarella | |
| 2018/0289223 A1 | 10/2018 | Harris | |
| 2019/0159636 A1 | 5/2019 | Lo | |
| 2019/0298115 A1 | 10/2019 | Ciavarella | |
| 2019/0357735 A1 | 11/2019 | Wise | |
| 2020/0069761 A1* | 3/2020 | Mouser | A61K 31/4166 |
| 2020/0253198 A1* | 8/2020 | Hillman | A01N 25/30 |

FOREIGN PATENT DOCUMENTS

| | | |
|---|---|---|
| CN | 103742391 A | 4/2014 |
| CN | 203570550 U | 4/2014 |
| CN | 203867833 U | 10/2014 |
| CN | 204003387 U | 12/2014 |
| EP | 2135538 A1 | 12/2009 |
| EP | 3064114 A1 | 9/2016 |
| JP | 2004301300 A | 10/2004 |
| JP | 2013133716 A | 7/2013 |
| JP | 2013133754 A | 7/2013 |
| WO | 2012154642 A1 | 11/2012 |
| WO | 2013126696 A2 | 8/2013 |

OTHER PUBLICATIONS

Notice of Allowance for U.S. Appl. No. 15/369,007 dated May 22, 2018.
Notice of Allowance for U.S. Appl. No. 15/356,795 dated May 21, 2018.
Notice of Allowance for U.S. Appl. No. 15/350,190 dated May 8, 2018.
Office Action for U.S. Appl. No. 15/480,711 dated Mar. 28, 2018.
Office Action for U.S. Appl. No. 15/355,112 dated Dec. 29, 2017.
Office Action for U.S. Appl. No. 15/369,007 dated Dec. 29, 2017.
Office Action for U.S. Appl. No. 15/356,795 dated Jan. 12, 2018.
Office Action for U.S. Appl. No. 15/350,190 dated Dec. 18, 2017.
Notice of Allowance for U.S. Appl. No. 15/350,185 dated Dec. 13, 2017.
Office Action for U.S. Application No. 15/429,389 dated Feb. 23, 2018.

* cited by examiner

HIGH QUALITY NON-AEROSOL HAND SANITIZING FOAM

RELATED APPLICATIONS

The present application is a continuation of U.S. patent application Ser. No. 15/429,389 titled HIGH QUALITY NON-AEROSOL HAND SANITIZING FOAM, which was filed on Feb. 10, 2017 and, which will issue as U.S. Pat. No. 10,441,115 on Oct. 15, 2019, and which is incorporated herein by reference in its entirety.

In addition, the present application claims priority to and the benefits of U.S. Non-Provisional In addition, the present invention claims priority to, and the benefits of: U.S. Provisional Application Ser. No. 62/293,931 filed on Feb. 11, 2016 and titled HIGH QUALITY NON-AEROSOL HAND SANITIZING FOAM; U.S. Non-Provisional application Ser. No. 15/369,007 filed on Dec. 5, 2016 and titled SEQUENTIALLY ACTIVATED MULTI-DIAPHRAGM FOAM PUMPS, REFILL UNITS AND DISPENSER SYSTEMS; U.S. Provisional Application Ser. No. 62/319,061 filed on Apr. 6, 2016 and titled SEQUENTIALLY ACTIVATED MULTI-DIAPHRAGM FOAM PUMPS, REFILL UNITS AND DISPENSER SYSTEMS; U.S. Non-Provisional patent application Ser. No. 15/355,112 filed on Nov. 18, 2016 and titled SEQUENTIALLY ACTIVATED MULTI-DIAPHRAGM FOAM PUMPS, REFILL UNITS AND DISPENSER SYSTEMS; U.S. Non-Provisional application Ser. No. 15/356,795 filed on Nov. 21, 2016 and titled FOAM DISPENSING SYSTEMS, PUMPS AND REFILL UNITS HAVING HIGH AIR TO LIQUID RATIOS; and U.S. Non-Provisional application Ser. No. 15/350,190 filed on Nov. 14, 2016 and titled IMPROVED FOAMING CARTRIDGE. Each of which are incorporated herein by reference in their entirety.

TECHNICAL FIELD

The present invention relates generally to high quality improved foam hand sanitizer characteristics for foam pumps and foam dispenser systems and more particularly high quality improved non-aerosol foam hand sanitizing foam.

BACKGROUND OF THE INVENTION

Liquid dispenser systems, such as liquid soap and sanitizer dispensers, provide a user with a predetermined amount of liquid upon actuation of the dispenser. In addition, it is sometimes desirable to dispense the liquid in the form of foam by, for example, injecting air into the liquid to create a foamy mixture of liquid and air bubbles. Some liquids, such as, for example, alcohol-based liquids are difficult to foam because alcohol is a defoaming agent. Accordingly, obtaining a high quality alcohol based foam is difficult and requires enhance mixing. Prior art foam sanitizers are either aerosol based and non-aerosol based. Aerosol-based foam utilizes a pressurized propellant to mix with the liquid and dispense the foam. Non-aerosol based hand sanitizers require a pump. Conventional non-aerosol pumps for generating foam form the foam by pumping a liquid and air mixture through a foam cartridge. Conventional foam pumps and foam cartridges are manufactured by Albea Beauty Holdings S.A. formally manufactured by Rexam Airspray ("Albea"), and Ophardt Hygiene Technologies Inc ("Ophardt"). While these foam pumps foam certain alcohol formulations containing surfactants, such as silane, the quality of the foamed alcohol is not as high as the quality of foam produced using foam soap.

SUMMARY

Exemplary embodiments of high quality non-aerosol foam sanitizers are disclosed herein. An exemplary embodiment of high quality non-aerosol foam sanitizer includes a liquid mixture that includes an alcohol, water and a surfactant mixed with and entrapping ambient air to form a plurality of foam bubbles. More than about 50 percent of the foam bubbles in the high quality foam have a size of between about 50 µm and about 250 µm.

Another exemplary embodiment of a high quality non-aerosol foam sanitizer includes a liquid mixture that includes an alcohol, water and a surfactant mixed with and entrapping air to form a plurality of foam bubbles. The liquid mixture is passed through an non-aerosol foam pump to generate foam and the average diameter of the foam bubbles are less than about 190 µm.

Another high quality non-aerosol foam sanitizer includes a liquid mixture that includes an alcohol, water and a surfactant mixed with and entrapping air to form a plurality of foam bubbles, wherein the maximum diameter of the foam bubbles are less than about 580 µm.

Another high quality non-aerosol foam sanitizer includes a liquid mixture that includes an alcohol, water and a surfactant mixed with and entrapping air to form a plurality of foam bubbles, wherein the mean bubble diameter is between about 100 µm and about 200 µm.

Another high quality non-aerosol foam sanitizer includes a liquid mixture that includes an alcohol, water and a surfactant mixed with and entrapping air to form a plurality of foam bubbles, wherein the average bubble size diameter is less than about 200 µm and the standard deviation of bubble diameters is less than about 100 µm.

An exemplary non-aerosol foam pump for producing high quality foam sanitizer includes a liquid pump portion for pumping a foamable sanitizer containing alcohol, water and a surfactant, two or more air pump portions and a mixing chamber for mixing the foamable sanitizer with the air to form a foam having foam bubbles. More than about 50 percent of the foam bubbles have a size of less than about 250 µm.

Another exemplary non-aerosol foam sanitizer includes a mixture of alcohol, water, a surfactant and atmospheric air. The mixture is mixed together to form a foam containing a plurality of bubbles. The plurality of bubbles have an average bubble size of less than about 200 µm and the foam has a foam density of greater than 0.095 g/ml.

An exemplary process for preparing a non-aerosol hand sanitizing foam includes providing a foamable hand sanitizing composition that includes water, alcohol and a surfactant. Providing a non-aerosol foam pump, the non-aerosol foam pump includes a mixing chamber for mixing the foamable hand sanitizing composition with atmospheric air. The non-aerosol foam pump pumps liquid and atmospheric air into the mixing chamber to mix together to form a foam. The foam is made of bubbles wherein the average bubble size is less that about 200 µm. The process further includes a foam outlet for dispensing the foam.

DETAILED DESCRIPTION

The present application discloses exemplary embodiments of high quality foam sanitizer that is an improvement over presently available foam sanitizers. Exemplary embodiments of the improved foam sanitizer exhibits reduced bubble size, more consistent bubble sizes, and is a more stable sanitizing foam.

Additionally, the present application discloses exemplary embodiments of sequentially activated multi-diaphragm foam pumps for use with the improved foaming cartridges as exemplary embodiments of foam pumps that are configured to provide high quality foam. Other foam pumps may be created that produce high quality foam that is disclosed and claimed herein. Without limiting effects, it is believed that some of the exemplary pumps disclosed herein are able to produce the high quality foam shown and described herein because they continually mix small amounts of liquid with small amounts of air. In addition, the pumps may force the air and liquid to mix and pass through the foaming cartridge at higher pressures. In addition, without limiting effect it is believed that the structure and configuration of the improved foaming cartridges may contribute to the high quality foam shown, described, and claimed herein.

Figure 1:
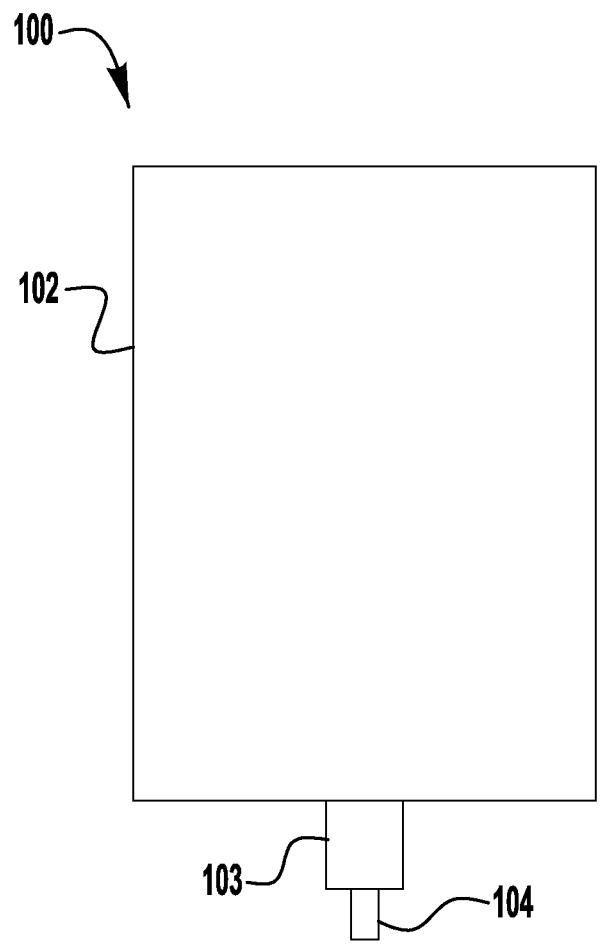
FIG. 1 is an exemplary embodiment of a refill unit for a foam dispenser that is configured to provide a high quality sanitizer foam.

FIGS. 1-14 discloses exemplary embodiments of non-aerosol foam pumps that are capable of producing the high quality foam bubbles disclosed and claimed herein. FIG. 1 illustrates a refill unit 100 for a foam dispenser for creating a high quality foam. The refill unit 100 includes a collapsible container 102. Collapsible container 102 includes a neck 103 and a drip-free quick connector 104. Exemplary drip-free quick connectors are disclosed in U.S. Pat. No. 6,871,679 titled Bag and Dispensing System Comprising Such A Bag, and U.S. Pat. No. 7,647,954 titled Connector Apparatus And Method For Connecting The Same For Controlling Fluid Dispensing, which are incorporated herein by reference in their entirety. Disposable refill units contain a supply of a foamable liquid. Most of the embodiments disclosed herein center around alcohol based sanitizers, however, in various embodiments, the contained foamable liquid could be for example a soap, a sanitizer, a cleanser, a disinfectant, a lotion or the like. The container is a collapsible container and can be made of thin plastic or a flexible bag-like material. In other embodiments, the container may be a non-collapsing container formed by a rigid housing member, or any other suitable configuration for containing the foamable liquid without leaking. In the case of a non-collapsing container, a vent system may be included. Exemplary venting systems are disclosed in U.S. Patent Applications Publication No. 2015/0266657 titled Closed System for Venting a Dispenser Reservoir; Publication No. 2015/025184 titled Pumps With Container Vents and application Ser. No. 14/811,995, titled Vented Refill Units And Dispensers Having Vented Refill Units, which are incorporated herein by reference.

Figure 2:
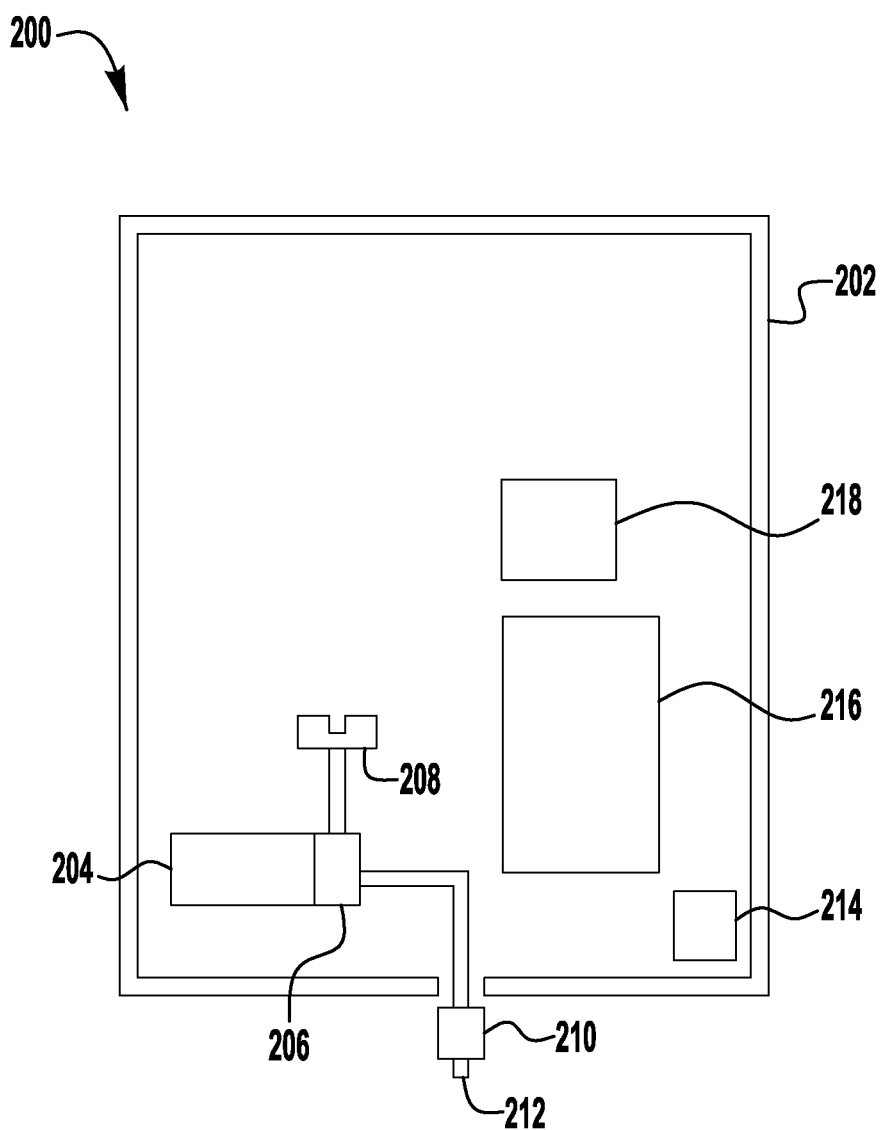
FIG. 2 is an exemplary embodiment of a foam dispenser that is configured to provide a high quality sanitizer foam.
Figure 2A:
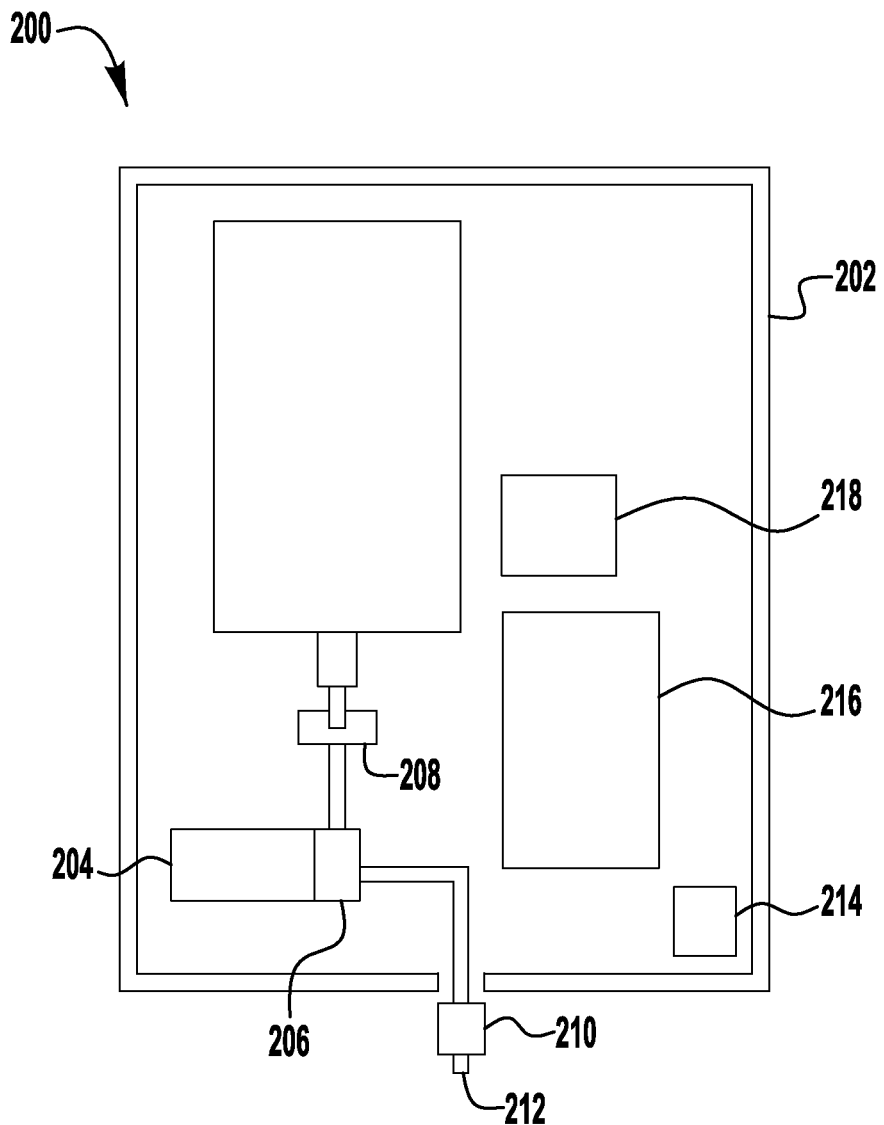
FIG. 2A is the exemplary foam dispenser of FIG. 2 with the exemplary refill unit of FIG. 1 installed.

FIG. 2 illustrates an exemplary embodiment of a touch-free foam dispenser 200 that is configured to provide high quality sanitizer foam. The touch-free foam dispenser 200 includes a housing 202, a motor 204, a foam pump 206, a refill unit connector 208, a foam cartridge 210, and a nozzle 212. Exemplary embodiments of foam cartridges 210 are shown and described below with respect to FIG. 13. A refill unit 100 may be connected to the refill unit connector 208 as shown in FIG. 2A. The refill unit 100 contains a foamable liquid, such as a soap, a sanitizer, a lotion, a cleanser, a disinfectant or the like. The touch-free foam dispenser 200 is activated when sensor 214 detects the presence of a user or object. Upon detection of an object or user, the sensor 214 provides a signal to the processor (not shown) in the electronic control board 216. The electronic control board 216 provides an output signal that causes the motor 204 to rotate an eccentric wobble plate actuator drive mechanism 301. The sensor 214 and the electronic control board 216 receive power from a power source 218. In some embodiments, the motor 204 receives power from the power source 218, and, in other embodiments, the refill unit includes a power source (not shown) that provides power to a rechargeable power source (not shown). Exemplary embodiments of refill units with power supplies that provide power to the wobble plate actuator drive mechanism 301 are shown and described in U.S. Publication No. 2014/0234140 titled Power Systems For Touch Free Dispensers And Refill Units Containing A Power Source, which is incorporated herein by reference in its entirety. Providing power to the motor 204 causes wobble plate actuator drive mechanism 301 to rotate. Rotation of wobble plate actuator drive mechanism 301 sequentially compresses and expands the diaphragms of foam pump 206 and pumps liquid and ambient air into mixing chamber 325. The liquid and air mix together and form a foam mixture. The foam mixture is forced through the foam cartridge 210, which creates a rich foam. The rich foam is dispensed from the foam dispenser 200 through the nozzle 212.

The refill unit 100 and the foam dispenser 200 illustrated in FIGS. 1 and 2, respectively, are drawn generically because a variety of different components may be used for many of the refill unit 100 and the foam dispenser 200. Although foam pump 206 is illustrated generically above, it is described in detail below. Some exemplary dispenser components that may be used in accordance with the present invention are shown and described in U.S. Pat. No. 8,960,498 titled Touch-Free Dispenser With Single Cell Operation And Battery Banking; U.S. Pat. Pub. No. 2014/00543.22 titled Off-Axis Inverted Foam Dispensers And Refill Units and Pub. No. 2014/0234140 titled Power Systems For Touch Free Dispensers And Refill Units Containing A Power Source, which are incorporated herein by reference in their entirety.

Figure 3:
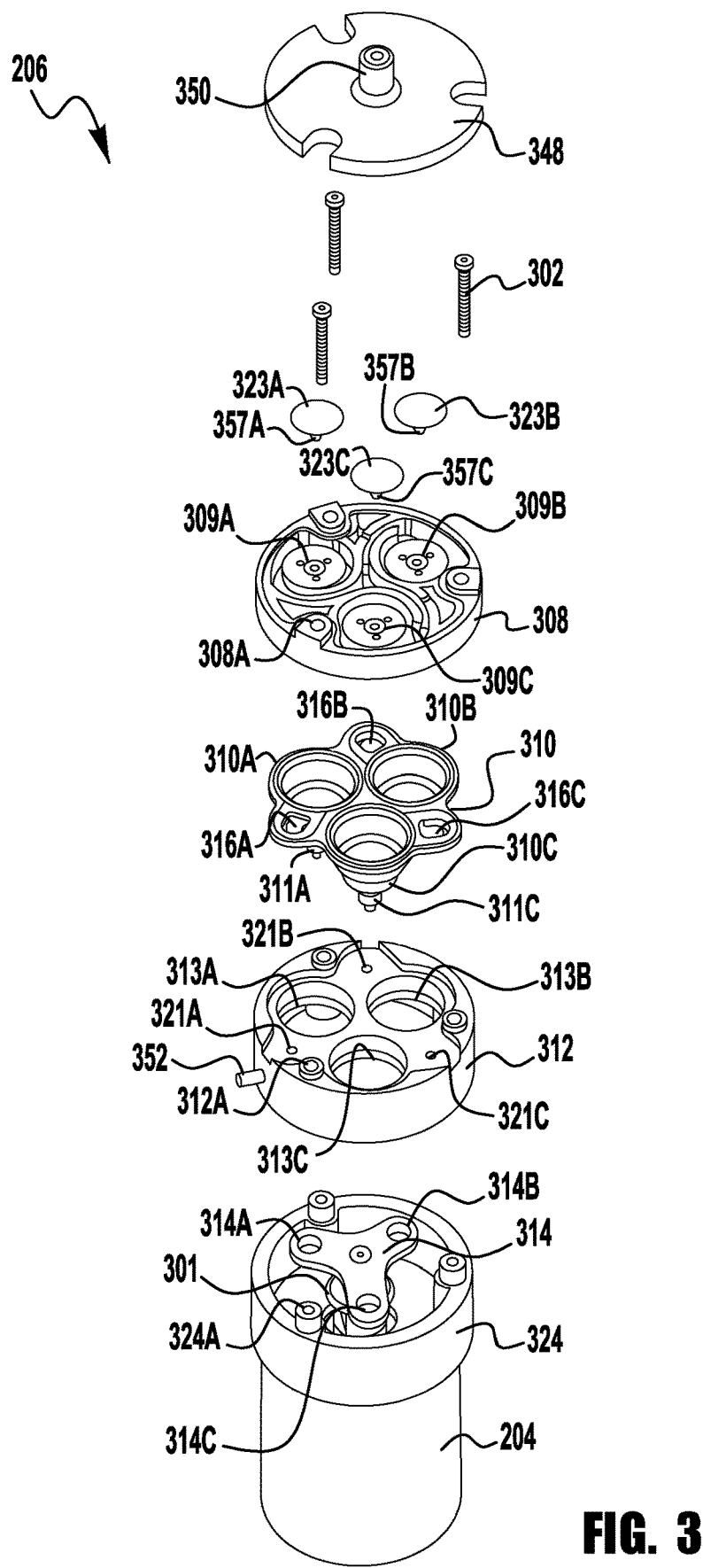
FIG. 3 is an exploded view of an exemplary embodiment of a sequentially activated multi-diaphragm foam pump that is configured to provide a high quality foam sanitizer taken from a first perspective.

FIG. 3 is an exploded view of an exemplary embodiment of foam pump 206 that is configured to provide a high quality foam sanitizer. Foam pump 206 is driven by motor 204. Foam pump 206 includes a pump base 324, a wobble plate 314, a diaphragm assembly seat 312, a diaphragm assembly 310, a valve seat 308, outlet valves 323A, 323B, 323C, screws 302, and a cover 348. The valve seat 308, diaphragm assembly seat 312, and pump base 324 are secured together by screws 302 in screw holes 308A, 312A, 324A. The cover 348 is attached to the valve seat 308. Outlet valves 323A, 323B 323C are secured to and seated in the valve seat 308.

The diaphragm assembly 310 includes three pump diaphragms 310A, 310B, 310C, and each pump diaphragm 310A, 310B, 310C has a connector 311A, 311B, 311C. The diaphragm assembly 310 is located in the diaphragm assembly seat 312. The pump diaphragms 310A, 310B, 310C are disposed in the receiving holes 313A, 313B, 313C of the diaphragm assembly seat 312, and the three connectors 311A, 311B, 311C connect to the wobble plate 314 by inserting the three connectors 311A, 311B, 311C in the three wobble plate links 314A, 314B, 314C.

Ambient air enters the foam pump 206 through pump air inlet 424B (FIG. 4), and liquid, such as for example, foamable soap or sanitizer enters the foam pump 206 through liquid inlet 352. Two of the pump diaphragms 310B, 310C receive ambient air, and the other pump diaphragm 310A receives foamable liquid, such as, for example soap or sanitizer.

Figure 4:
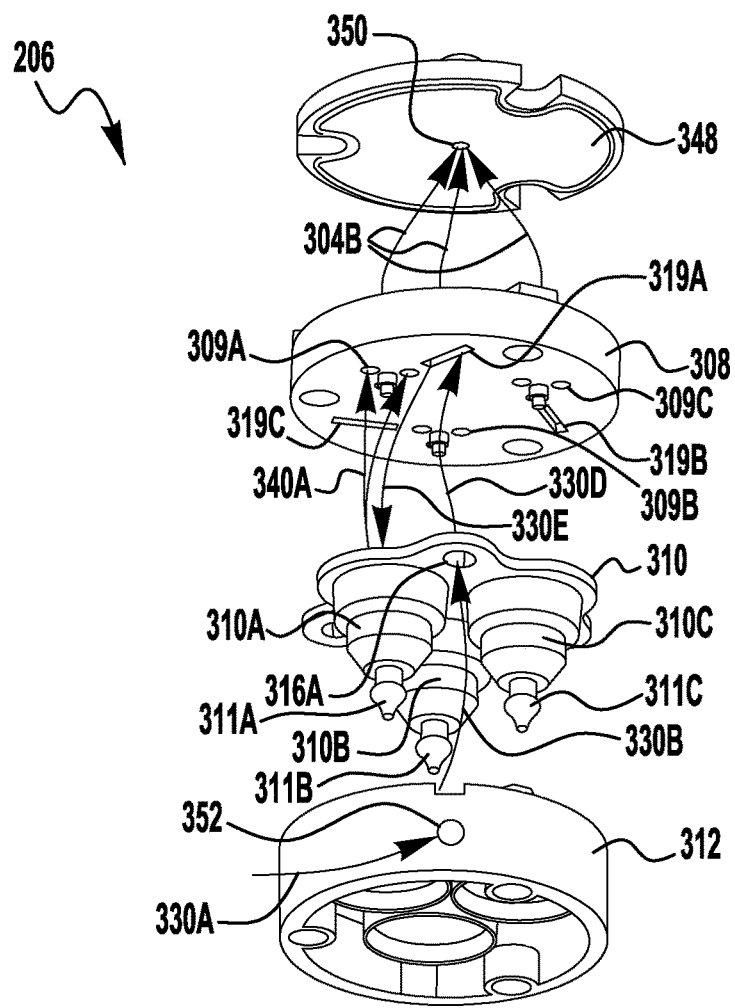
FIG. 4 is an exploded view of the exemplary embodiment of the sequentially activated multi-diaphragm foam pump of FIG. 3 taken from a second perspective.
Figure 4:
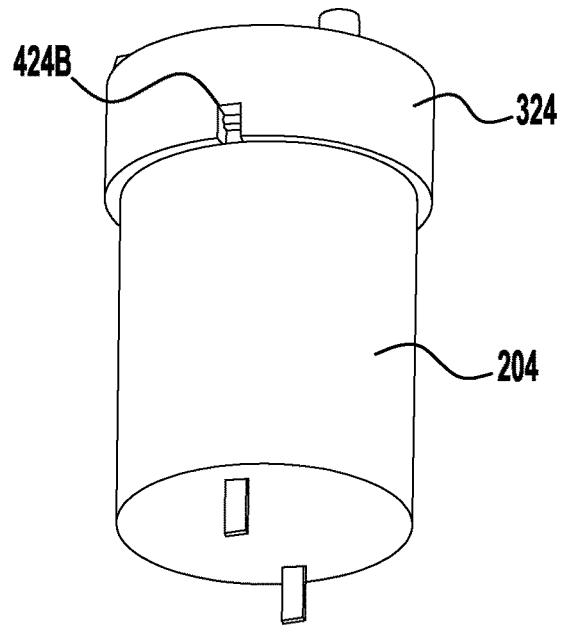

FIG. 4 is another exploded view of the exemplary foam pump 206 from a different perspective. As described above, the diaphragm assembly 310 includes three pump diaphragms 310A, 310B, 310C. Each pump diaphragm 310A, 310B, 310C has a corresponding inlet valve 316A, 316B, 316C (better seen in FIGS. 5 and 6). FIG. 4 also provides a view of the bottom of the valve seat 308. The bottom of valve seat 308 has three areas that correspond to the three pump diaphragms 310A, 310B, 310C. Each area has three fluid outlet apertures 309A, 309B, 309C that extend through valve seat 308, a valve stem retention aperture 329A, 329B, 329C (FIG. 7), and a fluid inlet groove 319A, 319B, 319C. The fluid inlet grooves 319A, 319B, 319C do not extend through valve seat 308.

Figure 5:
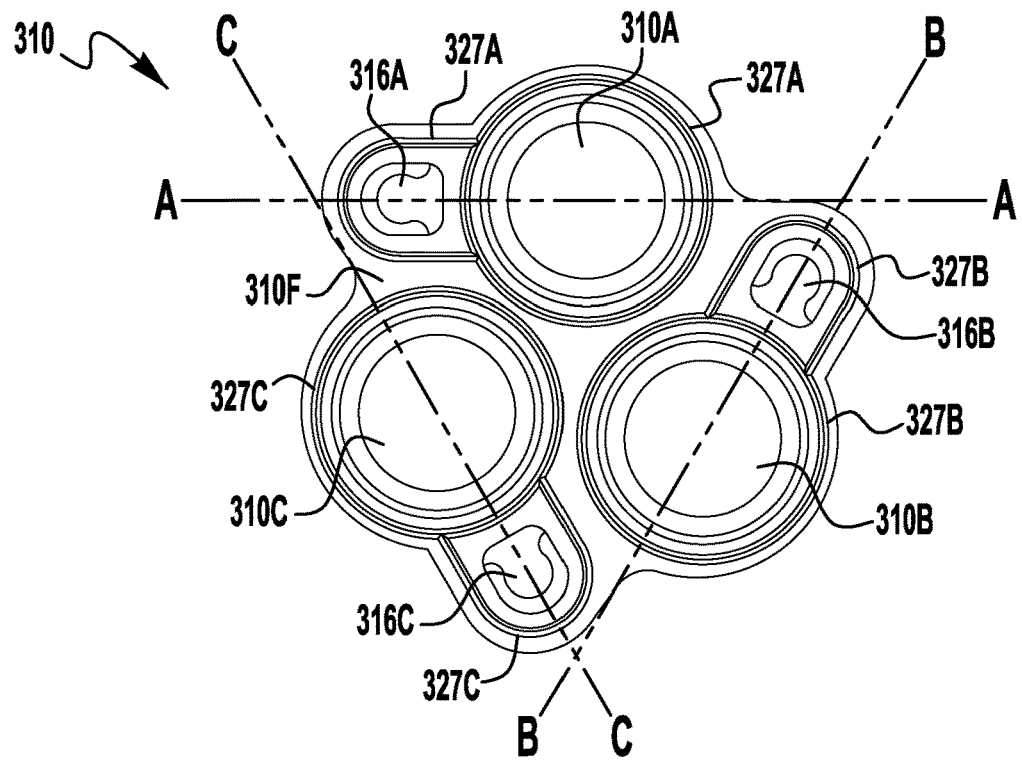
FIG. 5 is a top view of an exemplary diaphragm assembly for the exemplary embodiment of the sequentially activated multi-diaphragm foam pump of FIG. 3.
Figure 6:
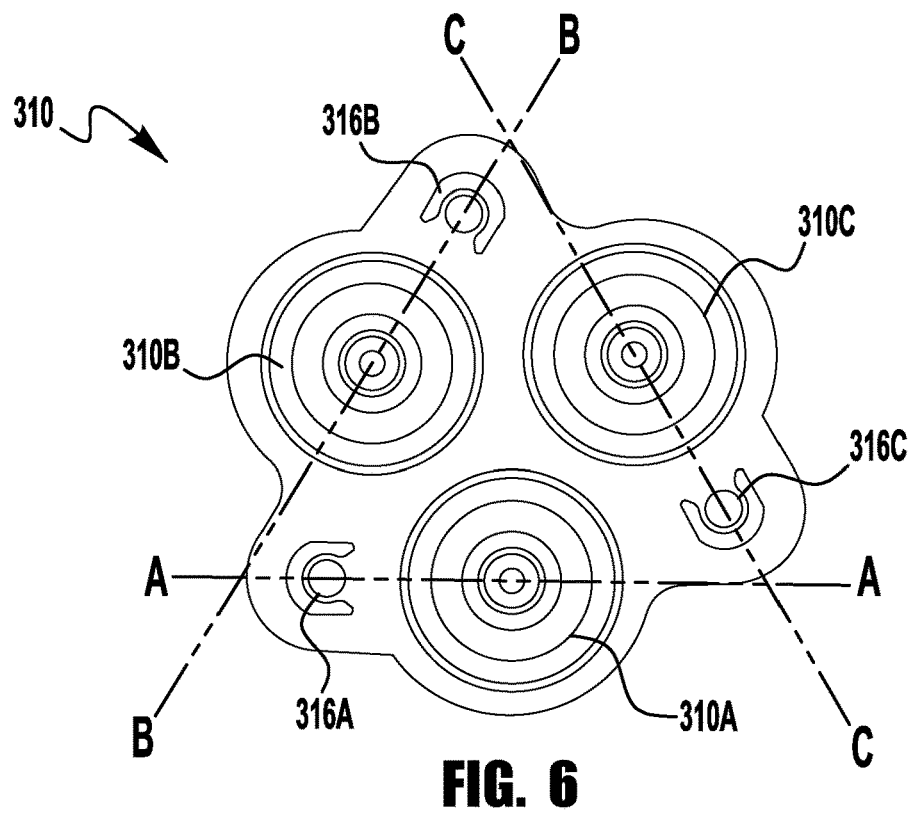
FIG. 6 is a bottom view of the exemplary diaphragm assembly for the exemplary embodiment of the sequentially activated multi-diaphragm foam pump.

FIGS. 5 and 6 illustrate a top view and a bottom view, respectively, of the exemplary diaphragm assembly 310 for foam pump 206. In some embodiments, the diaphragm assembly is made of natural rubber, EPDM, Silicone, Silicone rubber TPE, TPU, TPV, vinyl, or the like. The diaphragm assembly 310 includes three molded pump diaphragms 310A, 310B, 310C and three corresponding inlet valves 316A, 316B, 316C. The top of the diaphragm assembly 310 acts as a sealing gasket. The top of the diaphragm assembly 310 has a flat section 310F, and each pump diaphragm 310A, 310B, 310C has gasket walls 327A, 327B, 327C that surround the respective valves 316A, 316B, 316C and pump diaphragms 310A, 310B, 310C. The gasket walls 327A, 327B, 327C seal against the bottom of the valve seat 308 (FIG. 4 and FIG. 8) to prevent fluid, such as, air and liquid soap or sanitizer from leaking out of the foam pump 206 at a location other than the pump outlet 350 (FIG. 3). One-way inlet valves 316A, 316B, 316C allow ambient air, liquid soap, or sanitizer to enter the pump diaphragms 310A, 310B, 310C when the pump diaphragms 310A, 310B, 310C have a negative pressure (i.e., when the pump diaphragms 310A, 310B, 310C are expanding), and seal against inlet apertures 321A, 321B, 321C when the pump diaphragms 310A, 310B, 310C have a positive pressure (e.g. when the pump diaphragms 310A, 310B, 310C are compressing). The one-way inlet valves 316A, 316B, 316C are formed by flexible tabs and are made of the same material as the diaphragm assembly 310.

Figure 7:
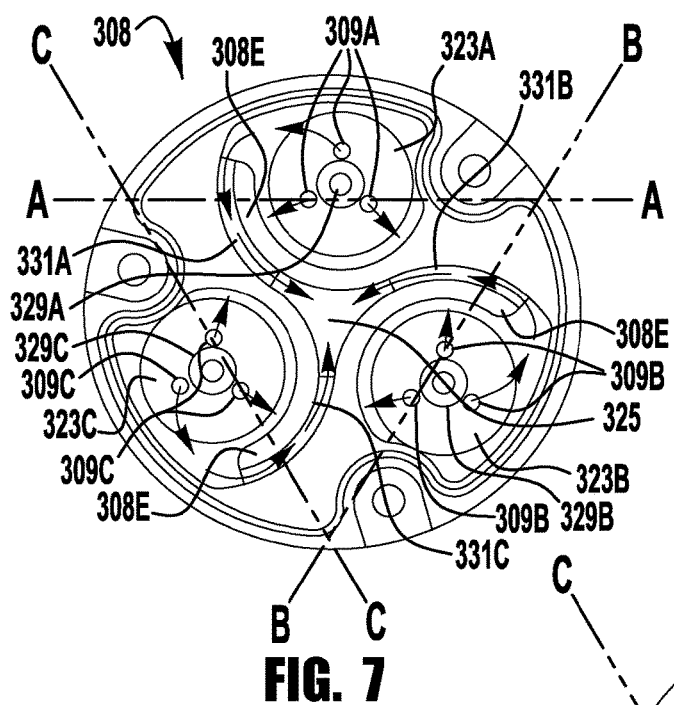
FIG. 7 is a top view of an exemplary valve seat for the exemplary embodiment of the sequentially activated multi-diaphragm foam pump of FIG. 3.

FIG. 7 is a top view of an exemplary valve seat 308 for the foam pump 206. One-way liquid outlet valve 323A is shown transparently to more clearly illustrate the flow of liquid 331A through liquid outlet apertures 309A and into mixing chamber 325. One-way liquid outlet valve 323A includes a valve stem 357A (FIG. 3) that is inserted into aperture 329A to secure one-way liquid outlet valve 323A to valve seat 308. One-way liquid outlet valve 323A is normally closed and prevents air or liquid from flowing from the mixing chamber 325, back through air outlet apertures 309A, and into liquid pump diaphragm 310A. One-way liquid outlet valve 323 opens when liquid pump diaphragm 310A is being compressed to pump fluid.

Similarly, one-way air outlet valves 323B, 323C are shown transparently to more clearly illustrate the flow of air 331B, 331C through air outlet apertures 309B, 309C and into mixing chamber 325. One-way air outlet valves 323B, 323C each include a valve stem 357B, 357C (FIG. 3) that are inserted into corresponding apertures 329B, 329C to secure the one-way air outlet valves to valve seat 308. One-way air outlet valves 323B, 323C are normally closed and prevent air or liquid from flowing from the mixing chamber 325, back through air outlet apertures 323B, 323C, and into air pump diaphragms 310B, 310C. One-way air outlet valves 323B, 323C open when corresponding air pump diaphragms 310B, 310C are being compressed to pump air.

The valve seat 308 also includes flow directional control walls 308E. The flow directional control walls 308E provide flow paths that aid in the mixing of liquid and air. In this embodiment the flow directional control walls 308E are curved and cause the liquid and air to intersect in a tangential relationship. In some embodiments, flow directional control walls 308E are designed and arranged to cause the liquid an air to intersect at a desired angle, such as, for example, each flow path may intersect at a 120 degree angle. In some embodiments, the flow directional control walls 308E are arranged so that the two air paths intersect the liquid flow path at about 180 degrees. The design of the flow path intersection may be different for different types of liquids, for example, a higher quality of foam may be obtained by causing the liquid soap to be intersected head on (180 degrees) by the two air flow paths, while a higher quality foam may be obtained for foamable sanitizer by having the air paths tangentially intersect with the liquid path.

Figure 8:
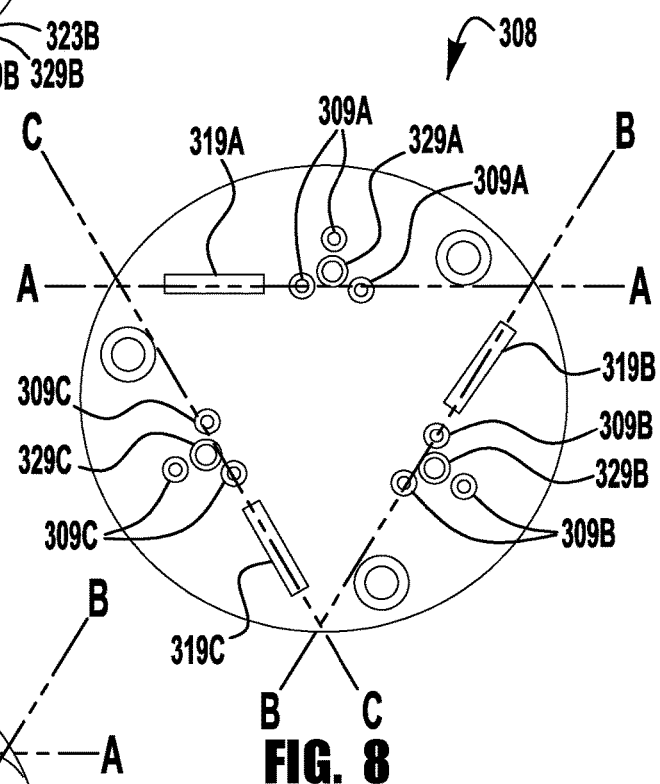
FIG. 8 is a bottom view of the exemplary valve seat of FIG. 7.

FIG. 8 is a bottom view of the exemplary valve seat 308 for the foam pump 206. The valve seat 308 includes three liquid outlet apertures 309A that pass through valve seat 308 and a liquid outlet valve aperture 329A for retaining one-way liquid outlet valve 323A. Valve seat 308 also includes a liquid inlet groove 319A that extends partially into valve seat 308 to provide a liquid path from one-way liquid inlet valve 316A to the interior of liquid pump diaphragm 310A. In addition, the valve seat 308 includes a first set of three air outlet apertures 309B that pass through valve seat 308, and a second set of three air outlet apertures 309C that pass through valve seat 308. Also, valve seat 308 includes air outlet valve apertures 329B, 329C for retaining one-way air outlet valves 323B, 323C, and air inlet grooves 319B, 319C that extend partially into valve seat 308 to provide an air path from one-way air inlet valves 316B, 316C to the interior of air pump diaphragms 310B, 310C.

Figure 9:
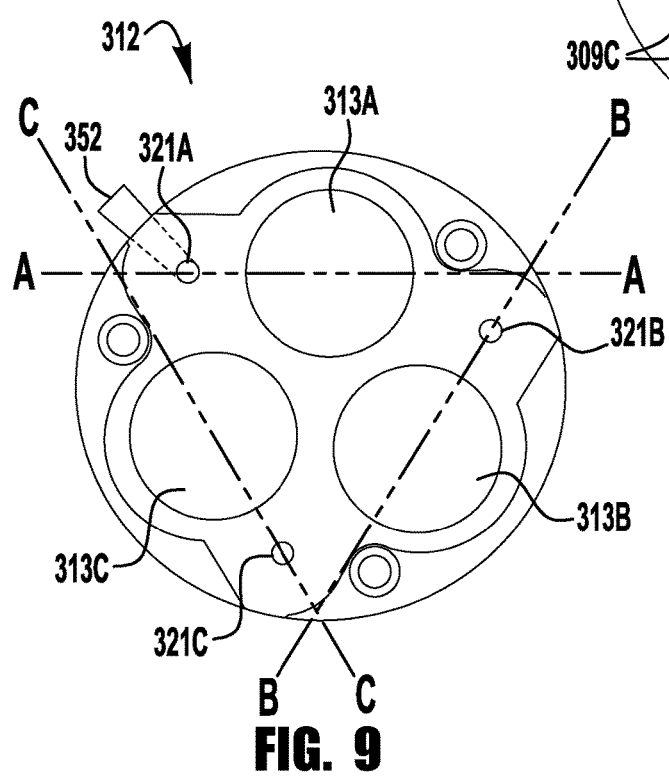
FIG. 9 is a top view of an exemplary diaphragm assembly seat for the exemplary embodiment of the sequentially activated multi-diaphragm foam pump of FIG. 3.

FIG. 9 is a top view of an exemplary diaphragm assembly seat 312 for the exemplary embodiment of a foam pump 206. The diaphragm assembly seat 312 includes three receiving holes 313A, 313B, 313C and three inlet apertures 321A, 321B, 321C. In fluid communication with inlet aperture 321A is fluid inlet 352 which may be coupled to the liquid outlet of container 102. Each receiving hole 313A, 313B, 313C is sized to receive a diaphragm 310A, 310B, 310C. Each inlet aperture 321A, 321B, 321C extends through diaphragm assembly seat 312 and allows either ambient air, liquid soap, or sanitizer to enter one of the diaphragms 310A, 310B, 310C.

Figure 10A:
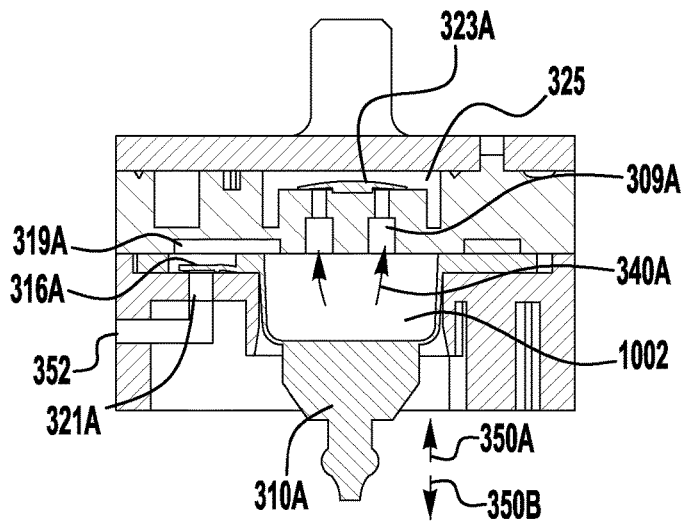
FIG. 10A is a cross-sectional view taken along the lines A-A of FIGS. 5-9 of a liquid pump portion of the sequentially activated multi-diaphragm foam pump.

FIG. 10A is a cross-sectional view taken along the lines A-A of FIGS. 5-9 showing the liquid pump portion of foam pump 206. In operation, liquid pump diaphragm 310A is moved downward, as shown by reference number 350B, to expand pump chamber 1002, which causes liquid inlet valve 316A to open allowing liquid to be drawn into pump chamber 1002 through liquid inlet 352, inlet aperture 321A, and liquid inlet groove 319A. Once the pump chamber 1002 is expanded it is primed with liquid, such as, for example, liquid soap or sanitizer. When the liquid pump diaphragm 310A is compressed (i.e. the liquid pump diaphragm 310A moves in the direction shown by reference number 350A), the liquid is pumped in the direction shown by reference number 340A. The liquid travels through liquid outlet apertures 309A, past one-way liquid outlet valve 323A and into mixing chamber 325. One-way liquid outlet valve 323A is normally closed, but one-way liquid outlet valve 323A opens due to pressure caused by compressing liquid pump chamber 1002. One-way liquid outlet valve 323A prevents air or liquid from flowing back through liquid outlet apertures 309A and into liquid pump diaphragm 310A. Subsequently, the liquid pump diaphragm 310A begins to expand, which starts the process again by causing liquid inlet valve 316A to open, and liquid is drawn into liquid pump chamber 1002 through liquid inlet aperture 321A and liquid inlet groove 319A. A operating cycle of foam pump 206 includes one pump of liquid from liquid pump diaphragm 310A through liquid outlet apertures 309A, past liquid outlet valve 323A, and into mixing chamber 325 (FIG. 7) (followed by two pumps of air as described below).

Figure 10B:
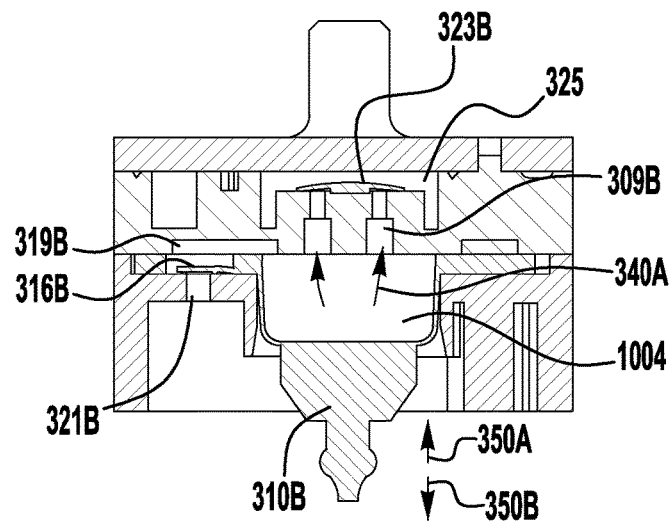
FIG. 10B is a cross-sectional view taken along the lines B-B of FIGS. 5-9 of an air pump portion of the sequentially activated multi-diaphragm foam pump.
Figure 10C:
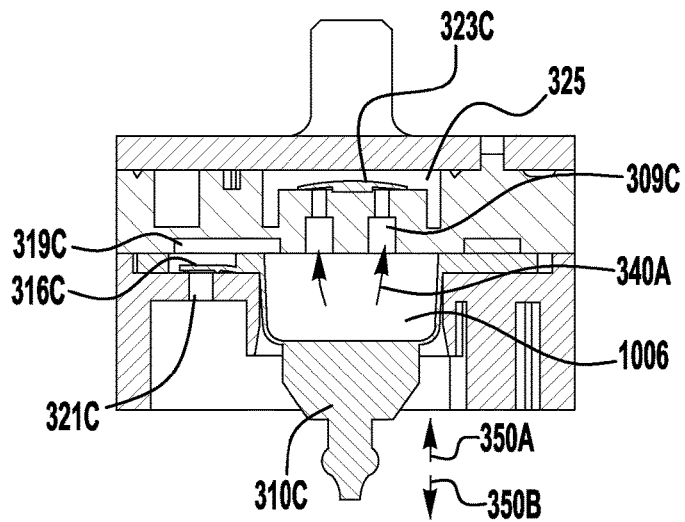
FIG. 10C is a cross-sectional view taken along the lines C-C of FIGS. 5-9 of a second air pump portion of the sequentially activated multi-diaphragm foam pump.

FIGS. 10B and 10C are a cross-sectional view taken along the lines B-B and C-C, respectively, of FIGS. 5-9 showing the air pump portions of foam pump 206. In operation, air pump diaphragms 310B, 310C are moved downward, as shown by reference number 350B, to expand air pump chambers 1004, 1006, which causes air inlet valves 316B, 316C to open allowing ambient air to be drawn into pump chambers 1004, 1006 through air inlet apertures 321B, 321C and air inlet grooves 319B, 319C. Once the pump chambers 1004, 1006 are primed with air, the air pump diaphragms 310B, 310C may be compressed (moved in the direction shown by reference number 350A). Compression of air pump diaphragms 310B, 310C pump the air in the direction shown by reference number 340A. The air travels through air outlet apertures 309B, 309C, past one-way air outlet valves 323B, 323C, and into mixing chamber 325 to mix with the foamable liquid. One-way air outlet valves 323B, 323C are normally closed, but one-way air outlet valves 323B, 323C open due to pressure caused by compressing air pump chambers 1004, 1006. One-way air inlet valves 323B, 323C prevent air or liquid from flowing back through air outlet apertures 309B, 309C and into air pump diaphragms 310B, 310C. Subsequently, the air pump diaphragms 310B, 310C begin to expand, which starts the process again by causing air inlet valves 316B, 316C to open, and ambient air is drawn into air pump chambers 1004, 1006 through air inlet apertures 321B, 321C and air inlet grooves 319B, 319C. An operating cycle of foam pump 206 includes one pump of liquid (as described above) followed by one pump of air from air pump diaphragm 310B through air outlet apertures 309B, past air outlet valve 323B, and into mixing chamber 325 (FIG. 7). In addition, an operating cycle of foam pump 206 includes one pump of ambient air from air pump diaphragm 310C through air outlet apertures 309C, past air outlet valve 323C, and into mixing chamber 325 (FIG. 7).

The diaphragms 310A, 310B, 310C operate sequentially, in which one sequence of operation includes one pump of liquid, such as, for example, soap or sanitizer, or ambient air by each of the three pump diaphragms 310A, 310B, 310C. The order of operation of the pump diaphragms 310A, 310B, 310C is dependent upon the configuration of the wobble plate 314 (FIG. 3). As shown in FIG. 3, each pump diaphragm 310A, 310B, 310C has a connector 311A, 311B, 311C, and the three pump diaphragms 310A, 310B, 310C connect to the wobble plate 314 by inserting the three connectors 311A, 311B, 311C in the three wobble plate links 314A, 314B, 314C. Wobble plate 314 connects to an eccentric wobble plate actuator that causes the wobble plate 314 to undulate. As the wobble plate 314 undulates, the wobble plate links 314A, 314B, 314C move in upward and downward motions. The upward motion causes the pump diaphragms 310A, 310B, 310C to compress, and the downward motion causes the pump diaphragms 310A, 310B, 310C to expand. The configuration of the wobble plate 314 causes one pump diaphragm 310A, 310B, 310C to compress at a time, which causes the pump diaphragms 310A, 310B, 310C to pump sequentially. The configuration of the wobble plate 314 also causes one pump diaphragm 310A, 310B, 310C to expand at a time, which causes the pump diaphragms 310A, 310B, 310C to prime sequentially. In the exemplary sequence of operation, the liquid pump diaphragm 310A pumps a shot of fluid, followed by air pump diaphragm 310B pumping a shot of air, and the sequence of operation ends with air pump diaphragm 310C pumping a second shot of air. The sequence may be repeated any number of times depending on the desired output dose of foam. The air from the air pump diaphragms 310B, 310C mixes with either the liquid or sanitizer from the liquid pump diaphragm 310A in the mixing chamber 325 (FIG. 7), which creates a foam mixture. The foam mixture exits the foam pump 206 through the pump outlet 350.

FIG. 4 illustrates the flow path of the liquid soap or sanitizer through the exploded view. When the liquid pump diaphragm 310A expands, liquid enters the foam pump 206 through liquid inlet 352, which is shown by reference number 330A. The liquid travels through aperture 321A in the diaphragm assembly seat 312, and past liquid one-way inlet valve 316A, as shown by reference number 330B. Inlet valve 316A opens, the liquid travels through groove 319A and into liquid pump diaphragm 310A, which is shown by reference numbers 330D and 330E.

The liquid pump diaphragm 310A compresses and pumps the liquid through liquid outlet aperture 309A, past one-way liquid outlet valve 323A, and into the mixing chamber 325 (FIG. 7), which is shown by reference number 340A. Air follows a similar path for air pump diaphragms 310B, 310C. When air pump diaphragms 310B, 310C expand, air is drawn into air inlet 424B, travels through apertures 321B, 321C (FIG. 9) in diaphragm seat assembly 312, travels through one-way air inlet valves 316B, 316C (FIGS. 5 and 6), travels into grooves 319B, 319C, in the bottom of valve seat 308, and travels into air pump diaphragms 310B, 310C. When air pump diaphragms 310B, 310C compress, air is forced through apertures 309B, 309C, past one-way air outlet valves 323B, 323C (FIG. 7), and into mixing chamber 325 where it mixes with the liquid to form a foam mixture. The foam mixture is dispensed through outlet 350, which is shown by reference number 304B.

Figure 11:
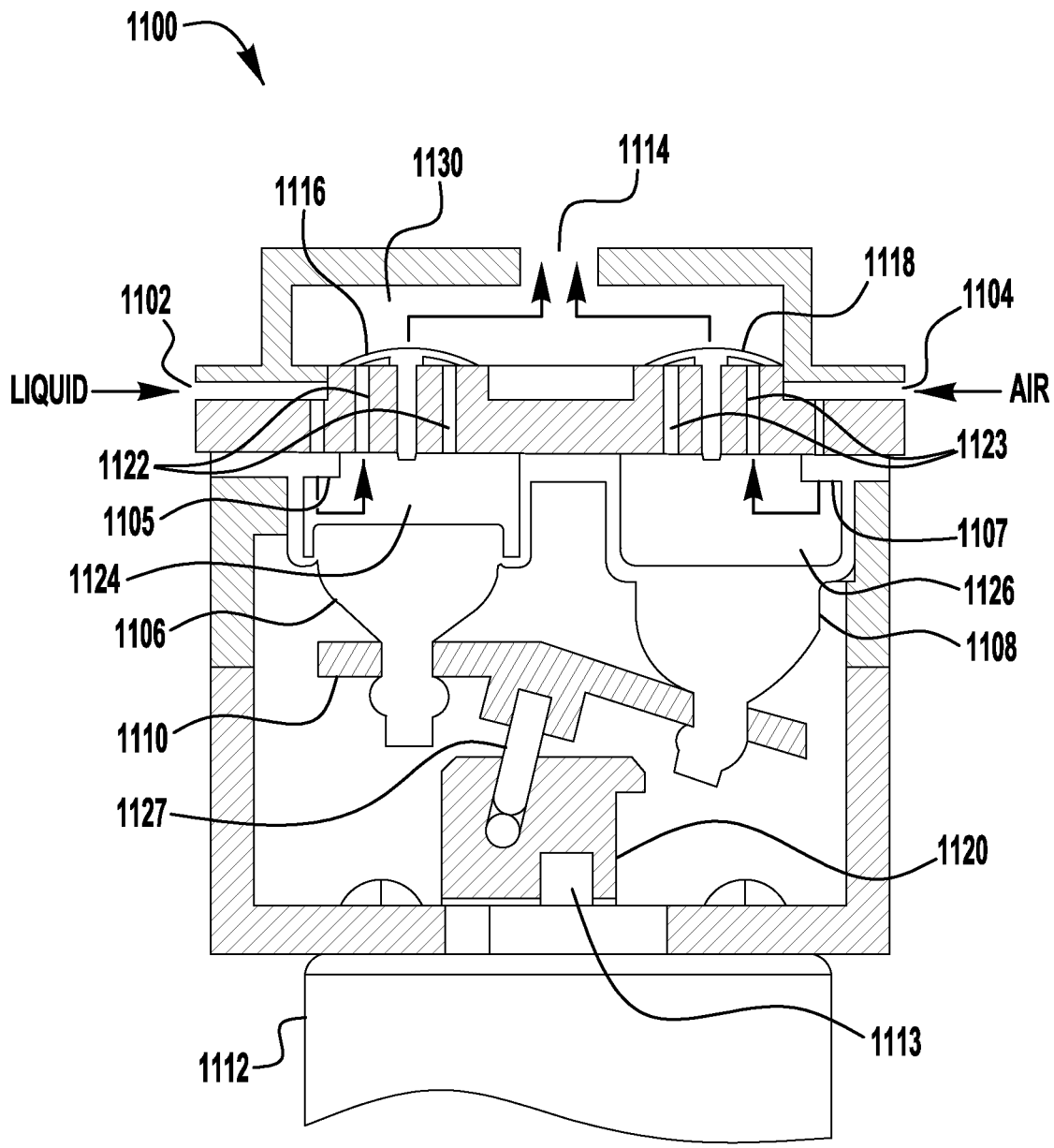
FIG. 11 is a cross-sectional view of another exemplary embodiment of a sequentially activated multi-diaphragm foam pump that is configured to provide a high quality foam sanitizer.

FIG. 11 is a cross-sectional view of another exemplary embodiment of a sequentially activated multi-diaphragm foam pump 1100 that is configured to provide a high quality foam sanitizer. The sequentially activated multi-diaphragm foam pump 1100 includes a motor 1112, a motor shaft 1113, a wobble plate 1110, a wobble plate pin 1127 an eccentric wobble plate drive 1120, a liquid pump diaphragm 1106, two air pump diaphragms 1108 (only one is shown), mixing chamber 1130, and pump outlet 1114. The motor 1112 drives the motor shaft 1113, which causes the motor shaft 1113 to rotate. The rotation of the motor shaft 1113 causes the eccentric wobble plate drive 1120 to rotate, and rotation of the eccentric wobble plate drive 1120 causes the wobble plate pin 1127 to move along a circular path, which causes the wobble plate 1110 to undulate. In some embodiments, wobble plate 314 includes a ball 1128 that rides in a socket (not shown) on the pump housing and wobble plate pin 127 extends outward and connects to an eccentric wobble plate actuator 1120 that causes the pin to move along a circular path which causes the wobble plate 1110 to undulate. As the wobble plate 1110 undulates, the ends connected to the three pump diaphragms 1106, 1108 move in upward and downward motions, and the three pump diaphragms 1106, 1108 are compressed sequentially. One sequence of operation of the mixing pump 1100 includes one pump by each of the three pump diaphragms 1106, 1108. The liquid pump diaphragm 1106 operates first in the cycle of operation, followed by sequential distributions by the two air pump diaphragms 1108.

Similar to the embodiments described above, during operation, the liquid pump diaphragm 1106 expands and contracts to pump liquid, and the air pump diaphragms 1108 (only one is shown) expand and contract to pump air. The expansion of the liquid pump diaphragm 1106 opens the liquid inlet valve 1105 and allows liquid, such as, for example, soap or sanitizer to enter liquid pump chamber 1124 through liquid inlet 1102. The expansion of the air pump diaphragms 1108 opens the air inlet valves 1107 (only one is shown) and allows air to enter air pump chambers 1126 (only one is shown) through air inlets 1104. Circular movement of the wobble plate pin 1127 causes the ends of the wobble plate 1110 to sequentially undulate. The undulation causes liquid pump diaphragm to compress, which causes liquid outlet valve 1116 to open, and liquid to flow into the mixing chamber 1130 through liquid outlet apertures 1122. Subsequently, one of the air pump diaphragms 1108 is compressed by the undulating wobble plate 1110, which causes air outlet valve 1118 to open, and air to flow the mixing chamber 1130 through air outlet apertures 1123. Then, the other air pump diaphragm (not shown) will compress and pump air into mixing chamber 1130. The air and liquid soap or sanitizer mix in the mixing chamber 1130 to create a foam mixture. The foam mixture exits the mixing pump 1100 through pump outlet 1114.

Figure 12:
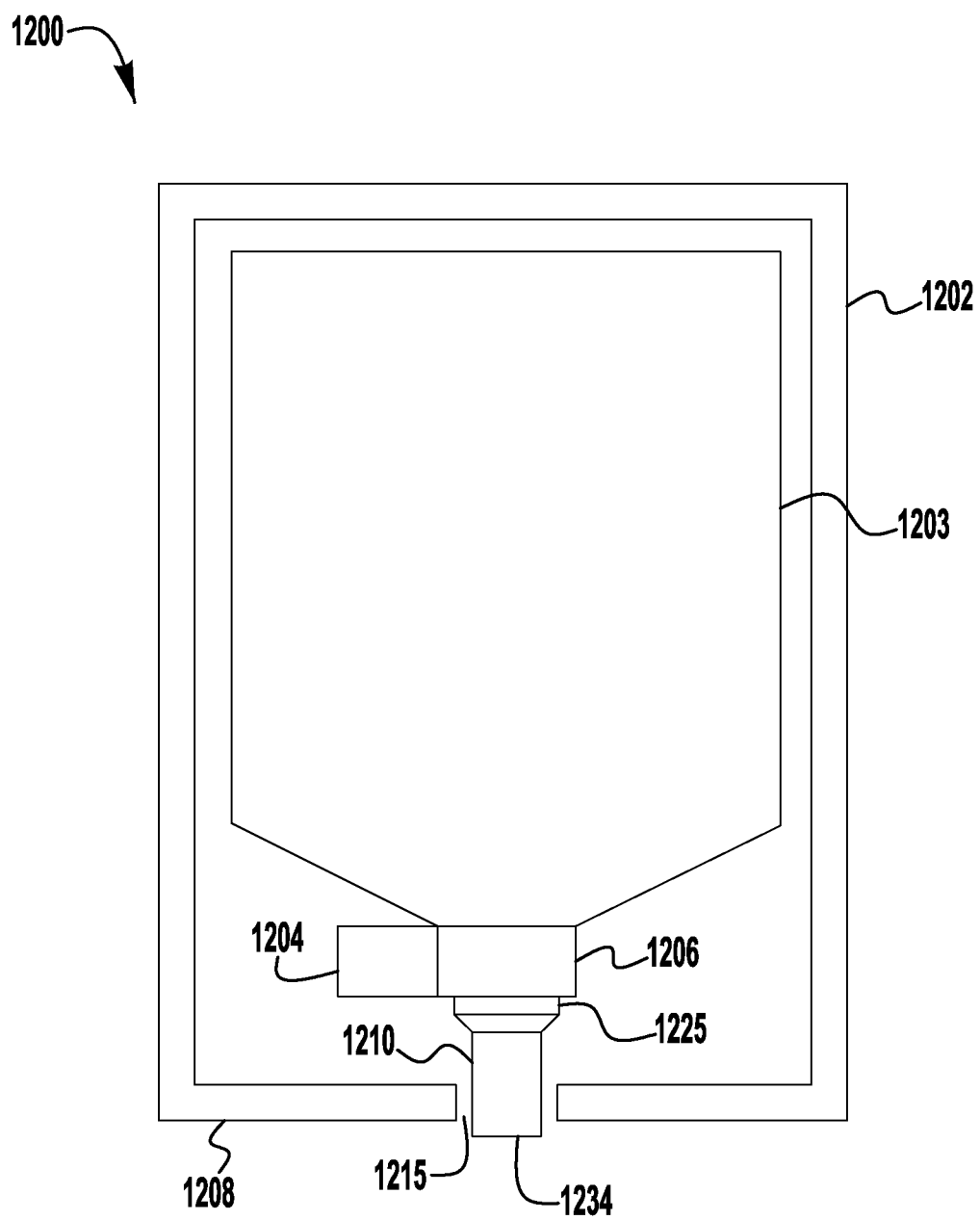
FIG. 12 is another exemplary embodiment of a foam dispenser.

FIG. 12 is another exemplary embodiment of a foam dispenser 1200 that is configured to provide a high quality foam sanitizer. The foam dispenser 1200 includes a housing 1202, a collapsible container 1203, an actuator 1204, a foam pump 1206, a foam cartridge 1210, and a nozzle 1234. The foam dispenser 1200 may be a wall-mounted system, a counter-mounted system, an un-mounted portable system movable from place to place, or any other kind of dispenser system. The foam dispenser may be include any of the types of pumps disclosed herein or incorporated herein by reference. Although most of the embodiments disclosed herein center around alcohol based sanitizers, in some embodiments, the collapsible container 1203 contains a foamable liquid, such as a soap, a sanitizer, a lotion, a cleanser, a disinfectant or the like. The actuator 1204 includes one or more parts that cause the foam dispenser 1200 to move liquid, air and/or foam. Actuator 1204 is generically illustrated because there are many different kinds of pump actuators 1204 which may be employed in dispenser 200. For example, actuator 1204 may be a manual lever, a manual pull bar, a manual push bar, a manual rotatable crank, an electrically activated actuator or any other means for actuating foam pump 1206. An electronic actuators may include a sensor (not shown) an electronic control board (not shown), a power source (not shown) and a motor 1204 such, as, for example, those shown in FIG. 2 and described above, to provide for a hands-free dispenser system with touch-less operation.

The foam pump 1206 is generically illustrated because there are many different kinds of foam pumps 1206 which may be employed in foam dispensers 1200. For example, the foam pump disclosed in U.S. Published Patent Application No. 2014/0367419 filed on Jun. 13, 2014 and entitled Foam Cartridges, Pumps, Refill Units And Foam Dispensers Utilizing the Same and U.S. Pat. No. 8,272,539 filed on Dec. 3, 2008 and entitled Angled Slot Foam Dispenser, which are incorporated by reference in their entirety, may be used in dispenser 100, or dispenser 1200. In addition, exemplary embodiments of sequentially activated multi-diaphragm foam pumps that are described in detail above, or incorporated herein, may be used in foam dispenser 100 or 1200.

The foam pump 1206 is in fluid communication with the container 1203 and an air inlet (not shown). The foam pump 1206 may be secured to the container 1203 by any means, such as, for example, a threaded connection, a welded connection, a quarter turn connection, a snap fit connection, a clamp connection, a flange and fastener connection, or the like. The foam pump 1206 is activated by actuator 1204, and the foam pump 1206 pumps liquid and air through mixing chamber 1225 and foam cartridge 1210. The foam cartridge 1210 is in fluid communication with the mixing chamber 1225. Foaming media are retained within the foam cartridge 1210. The foaming media generate foam from foamable liquid and air mixture. Some embodiments are especially well suited for enhanced foaming of foamable liquids containing alcohol. In an exemplary embodiment, the foaming media contains at least two sponges, an upstream sponge 1301A (FIG. 13) and a downstream sponge 1301B (FIG. 13) In the exemplary embodiment, the upstream sponge 1301A has a higher porosity than the downstream sponge 1301B.

Figure 13:
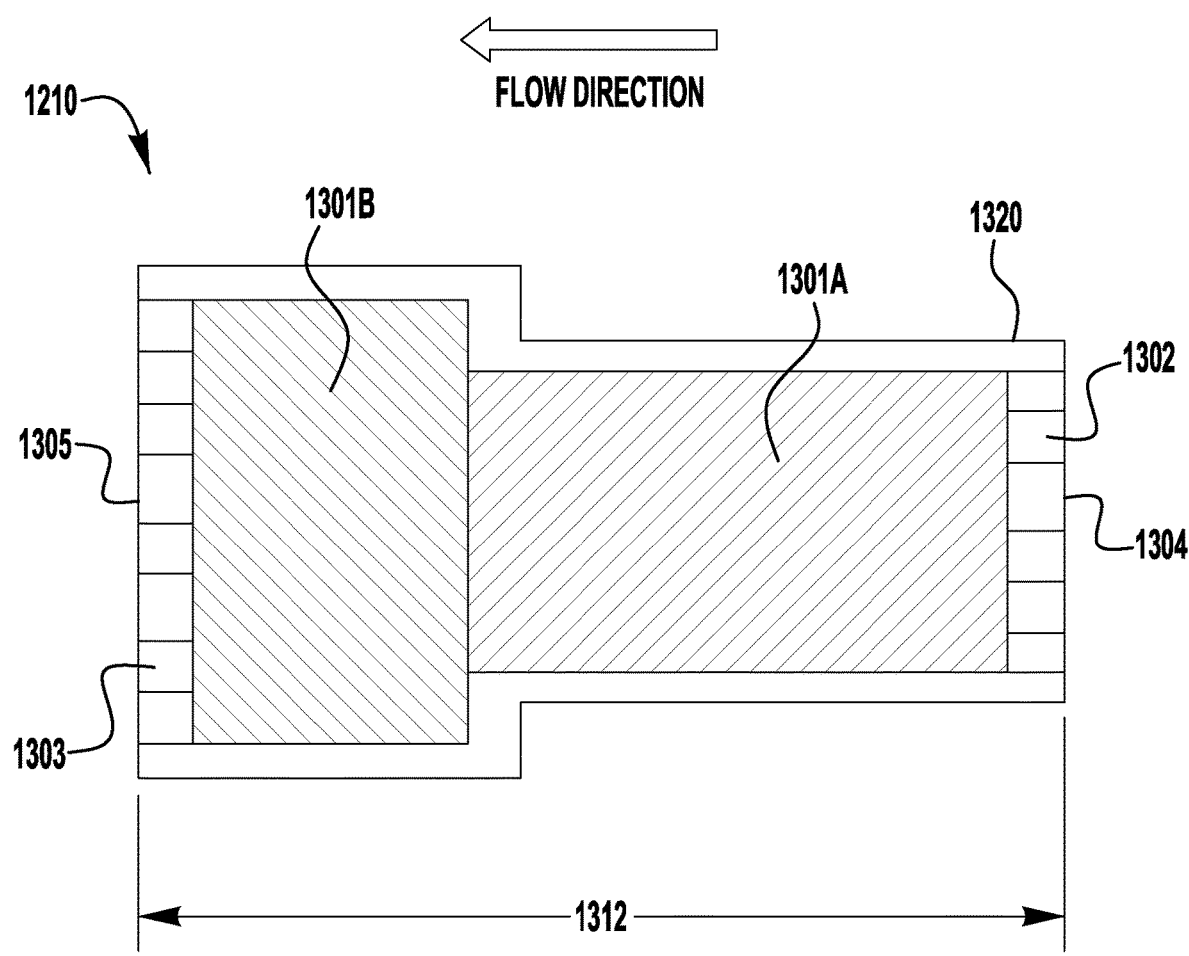
FIG. 13 is an exemplary embodiment of an improved foaming cartridge for a foam dispenser that is configured to provide a high quality foam sanitizer.

FIG. 13 is a cross-section of an exemplary foam cartridge 1210 for a foam dispenser 1200 that is capable of providing a high quality foam sanitizer. The foam cartridge 1210 includes a housing 1320 and a foaming stage 1312 with four foaming members. Housing 1320 has a first cross-sectional shape having a first diameter around the upstream sponge 1301A and a second cross-sectional shape having a second diameter around the downstream sponge 1301B. In the exemplary embodiment the second diameter is larger than the first diameter. The larger diameter of the housing 1320 and downstream sponge 1301B allow the foam/air mixture passing through the upstream sponge 1301A to expand into a larger area creating additional mixing of the air and liquid. Two of the four foaming members are sponges 1301A, 1301B. In the exemplary embodiment, the first foaming member is an inlet screen 1302. The second foaming member is upstream sponge 1301A. The third foaming member is downstream sponge 1301B. The fourth foaming member is outlet screen 1303. A mixture of air and liquid enters the foam cartridge 210 at inlet 1304 and is dispensed as rich foam from outlet 1305. After the mixture of air and liquid enters the inlet 1304, the mixture of air and liquid travels through the inlet screen 1302, which starts to enhance the foam. Next, the mixture of air and liquid travels through upstream sponge 1301A. Then, the mixture of air and liquid travels through downstream sponge 1301B. Finally, the mixture of air and liquid travels through outlet screen 1303 before exiting the foaming cartridge 1210 through outlet 1305 as rich foam. Foam cartridge 1210 may include a single foaming stage 1312 or several foaming stages. Also, the foaming cartridge 1210 may include several foaming members, with several different characteristics and configurations, disposed in the one or more foaming stages 1312.

The configuration of the foaming members in the foam cartridge 1210 may vary in different embodiments. In some embodiments, as shown in FIG. 13, the upstream sponge 1301A may be adjacent to the downstream sponge 1301B. In another embodiment, a space may exist between the upstream sponge 1301A and the downstream sponge 1301B. In another exemplary embodiment, a foaming member may be disposed between the upstream sponge 1301A and the downstream sponge 1301B.

In this exemplary embodiment, the foaming members include screens and sponges. Foaming members may include screens (1302, 1303), sponges 1301A, 1301B, other porous members (not shown), baffles (not shown), or the like. In the case of only two foaming members, some embodiments, include the upstream and downstream sponges 1301A, 1301B. Alternatively, there may be several foaming stages, and each includes at least two sponges 1301A, 1301B.

The characteristics of the foaming members in the foam cartridge 1210 may vary in different embodiments. In some embodiments, sponges 1301A, 1301B may be made of polyurethane reticulated foam. However, in other embodiments the sponges 401 may be made of reticulated polyester, reticulated polyether or polyether open pore foam. In some embodiments, the upstream sponge 1301A and downstream sponge 1301B may have the same porosities. In some embodiments, the upstream sponge 1301A and the downstream sponge 1301B may have different porosities. In some embodiments, the upstream sponge 1301A has a higher porosity than the downstream sponge 1301B. In some embodiments, the upstream sponge 1301A has a lower porosity than the downstream sponge 1301B. The porosity of sponges 1301A, 1301B may be defined as a function of the pores per inch of the sponges 1301A, 1301B and the amount of compression of the sponges 1301A, 1301B.

In some embodiments, the sponges 1301A, 1301B have the same amount of pores per inch and the porosity of the sponges 1301A, 1301B may be a function of the amount of compression of the sponges 1301A, 1301B. In some embodiments, the sponges 1301A, 1301B have between about 50 pores per inch and about 90 pores per inch. In some embodiments, the upstream sponge 1301A is compressed to between about 30 percent and about 50 percent of its uncompressed or relaxed state, and the downstream sponge 1301B is compressed to between about 60 percent and about 80 percent of its uncompressed or relaxed state. Accordingly, in this exemplary embodiment, the upstream sponge 1301A has a higher porosity than the downstream sponge 1301B because the upstream sponge 1301A is less compressed than the downstream sponge 1301B. Sponges 1301A, 1301B may have the same amount of pores per inch or different amounts of pores per inch, and sponges 1301A, 1301B may have the same amount of compression or a different amount compression. In addition, sponges 1301A, 1301B may have the same firmness or different firmness. Other materials that may be suitable for replacement of the sponges may include fabric felts, metal fibers, wax dipped paper filters etc.

In some embodiments, sponges 1301A, 1301B may be defined by firmness. Firmness is measure in pounds per square inch to cause a 25% deflection in the foam from its normal thickness. In some embodiments, the firmness is in the range of about 0.1 to about 2 pounds per square inch to achieve 25% deflection. In some embodiments, the sponges have a density in pounds/cubic foot, and have a density of less that about 4, including less than about 3.5, including less than about 3, including less than about 2.5.

Furthermore, in embodiments that include an inlet screen 1302 and an outlet screen 1303, the characteristics of the screens (1302, 1303) may vary. In some embodiments, the inlet screen 1302 has less threads per inch than outlet screen 1303, or vice versa. In an exemplary embodiment, the inlet screen 1302 has about 100 threads per inch, and the outlet screen 1303 has between about 150 threads per inch and about 200 threads per inch. However, screens 1302, 1303 may have the same number threads per inch. A foaming cartridge 1210 may have several screens 1302, 1303 in different locations throughout the foaming cartridge 210, and screens 1302, 1303 may have many variations in the amount of threads per inch. In addition, the screens 1302, 1303 and sponges 1301A, 1301B may be configured with spaces between the foaming members, with open spaces between two or more foaming members. The foaming members may be arranged as shown with a screen 1302 followed by sponges 1301A and 1301B followed by screen 1303, or arranged in various different orders.

Figure 14:
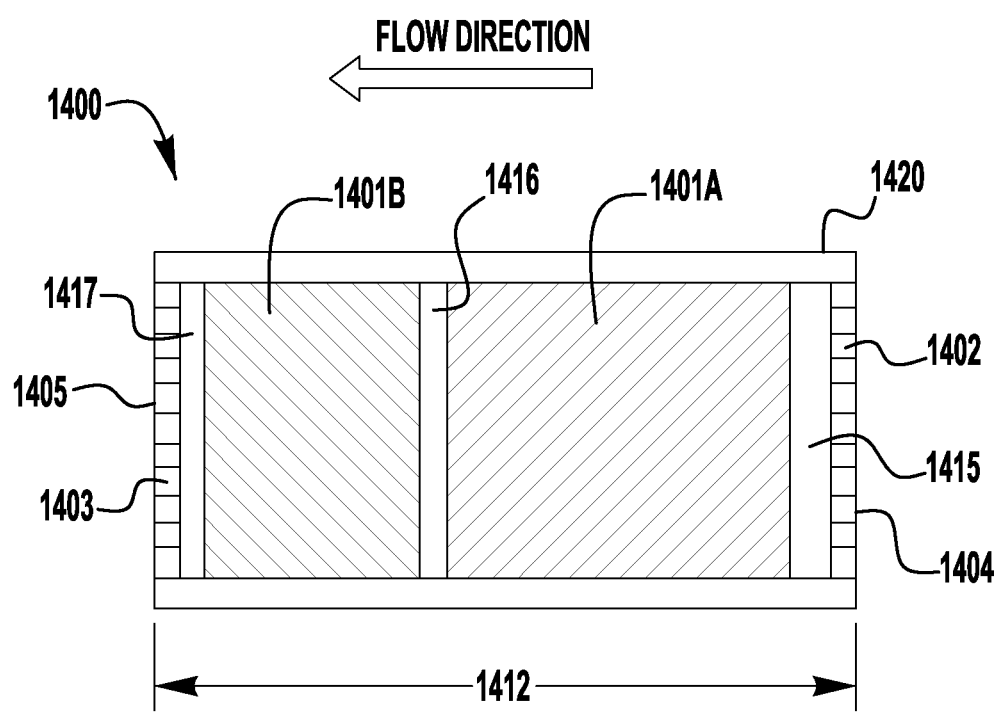
FIG. 14 is another exemplary embodiment of an improved foaming cartridge for a foam dispenser that is configured to provide a high quality foam sanitizer.

FIG. 14 is a cross-section of another exemplary foam cartridge 1400 for a foam dispenser 1200, which may be used in lieu of, or in combination with, foam cartridge 1210 and that is capable of providing a high quality foam sanitizer. Again, foam cartridge 1400 may be used with any of the pumps described herein or incorporated herein by reference. The foam cartridge 1400 includes a housing 1420 and a foaming stage 1412 with four foaming members. Two of the four foaming members are sponges 1401A, 1401B. In this exemplary embodiment, all of the foaming members have about the same diameter and housing 1420 has a cylindrical shape with a constant diameter. In the exemplary embodiment, the first foaming member is an inlet screen 1402. The second foaming member is upstream sponge 1401A. The third foaming member is downstream sponge 1401B. The fourth foaming member is outlet screen 1403. A mixture of air and liquid enters the foam cartridge 1400 at inlet 1404 and is dispensed as rich foam from outlet 1405. After the mixture of air and liquid enters the inlet 1404, the mixture of air and liquid travels through the inlet screen 1402, and into space 1415. Next, the mixture of air and liquid travels through upstream sponge 1401A and into space 1416. Then, the mixture of air and liquid travels through downstream sponge 1401B and into space 1417. Finally, the mixture of air and liquid travels through outlet screen 1403 and exits the foaming cartridge 1400 through outlet 1405 as rich foam. Foam cartridge 1400 may include a single foaming stage 1412 or several foaming stages. Also, the foaming cartridge 1400 may include several foaming members, with several different characteristics and configurations, disposed in the one or more foaming stages 1412.

The configuration of the foaming members in the foam cartridge 1400 may vary in different embodiments. In some embodiments, the upstream sponge 1401A may be adjacent to the downstream sponge 1401B. In some embodiments, a space may exist between the upstream sponge 1401A and the downstream sponge 1401B. In some embodiments, other foaming members may be disposed between the upstream sponge 1401A and the downstream sponge 1401B.

In this exemplary embodiment, the foaming members include screens and sponges. Optionally, foaming members may include screens (1402, 1403), sponges 1401A, 1401B, other porous members (not shown), baffles (not shown), or the like. In the case of only two foaming members, some embodiments, include the upstream and downstream sponges 1401A, 1401B. In some embodiments, there are two or more foaming stages, and each includes at least two sponges 1401A, 1401B.

The characteristics of the foaming members in the foam cartridge 1400 may vary in different embodiments. In some embodiments, sponges 1401A, 1401B may be made of polyurethane reticulated foam. In some embodiments the sponges 401 may be made of reticulated polyester, reticulated polyether or polyether open pore foam or the like. In some embodiments, the upstream sponge 1401A and downstream sponge 1401B may have the same porosities. In some embodiments, the upstream sponge 1401A and the downstream sponge 1401B may have different porosities. In some embodiments, the upstream sponge 1401A has a higher porosity than the downstream sponge 1401B. In some embodiments, the upstream sponge 1401A has a lower porosity than the downstream sponge 1401B. The porosity of sponges 1401A, 1401B may be defined as a function of the pores per inch of the sponges 1401A, 1401B and the amount of compression of the sponges 1401A, 1401B.

In some embodiments, the sponges 1401A, 1401B have the same amount of pores per inch and the porosity of the sponges 1401A, 1401B may be a function of the amount of compression of the sponges 1401A, 1401B. In some embodiments, the sponges 1401A, 1401B have between about 50 pores per inch and about 90 pores per inch. In some embodiments, the upstream sponge 1401A is compressed to between about 30 percent and about 50 percent of its uncompressed or relaxed state, and the downstream sponge 1401B is compressed to between about 60 percent and about 80 percent of its uncompressed or relaxed state. Accordingly, in this exemplary embodiment, the upstream sponge 1401A has a higher porosity than the downstream sponge 1401B because the upstream sponge 1401A is less compressed than the downstream sponge 1401B. Sponges 1401A, 1401B may have the same amount of pores per inch or different amounts of pores per inch, and sponges 1401A, 1401B may have the same amount of compression or a different amount compression. In addition, sponges 1401A, 1401B may have the same firmness or different firmness. Other materials that may be suitable for replacement of the sponges may include fabric felts, metal fibers, wax dipped paper filters etc.

In some embodiments, sponges 1401A, 1401B may be defined by firmness. Firmness is measure in pounds per square inch to cause a 25% deflection in the foam from its normal thickness. In some embodiments, the firmness is in the range of about 0.1 to about 2 pounds per square inch. In some embodiments, the sponges have a density in pounds/cubic foot, and have a density of less that about 4, including less than about 3.5, including less than about 3, including less than about 2.5. In some embodiments, the upstream sponge 1401A and downstream sponge 1401B may have the same firmness. In some embodiments, the upstream sponge 1401A and the downstream sponge 1401B may have different firmness. In some embodiments, the upstream sponge 1401A has a higher firmness than the downstream sponge 1401B. In some embodiments, the upstream sponge 1401A has a lower firmness than the downstream sponge 1401B.

Furthermore, in embodiments that include an inlet screen 1402 and an outlet screen 1403, the characteristics of the screens (1402, 1403) may vary. In some embodiments, the inlet screen 1402 have less threads per inch than outlet screen 1403, or vice versa. In an exemplary embodiment, the inlet screen 1402 has about 100 threads per inch, and the outlet screen 1403 has between about 150 threads per inch and about 200 threads per inch. However, screens 1402, 1403 may have the same threads per inch. A foaming cartridge 1400 may have several screens 1402, 1403 in different locations throughout the foaming cartridge 210, and screens 1402, 1403 may have many variations in the amount of threads per inch. In addition, the screens 1402, 1403 and sponges 1401A, 1401B may be configured with spaces between the foaming members (as shown), with open spaces between two or more foaming members. The foaming members may be arranged as shown with a screen 1402 followed by space 1415, followed by sponge 1401A followed by space 1416, followed by sponge 1401B, followed by space 1417 followed by screen 1403, or arranged in various different orders.

While the above-mentioned embodiments show and describe wall mounted and above counter mounted dispensers, the foam cartridges 1210, 1400 work very well with counter mount dispensers. An exemplary embodiment is shown and described in U.S. Pat. No. 8,544,698 filed on Mar. 26, 2007 and entitled Foam Dispenser with Stationary Dispense Tube which is incorporated herein in its entirety by reference.

It has been found that the pumps described herein and the foaming cartridges described herein in use with the pumps described herein or incorporated herein used alone or in combination produce a high quality sanitizer foam that is superior to the prior art pump products and foam cartridges. Alcohol is a deforming agent and it is difficult to create a rich or stable non-aerosol generated foam using alcohol based sanitizer formulations. It has been discovered that exemplary embodiments of foaming cartridges 1210, 1400 with two sponges having different porosities when used with foamable alcohol compositions and the diaphragm foam pumps described above provide a superior foam output over conventional foam pumps. It has also been discovered that exemplary embodiments of foaming cartridges 1210, 1400 with two sponges having different firmness when used with foamable alcohol compositions and the foam wobble pump described above provide a superior foam output over conventional foam pumps. In addition, it has also been discovered that the exemplary foaming cartridges improve the quality of foam in alcohol foam products when used with mini-foam pumps that have air and liquid pistons. It has also been found that the sequentially operated multi-diaphragm foam pumps disclosed and incorporated herein provide improved quality of foam in alcohol foam products.

Preferably, the hand sanitizing foams contain water, alcohol and a surfactant. Suitable alcohols may include lower alcohols, such as, for example, a c1-c8 alcohol, c1-c4 alcohol, or c2-c3 alcohol. Other alcohols may include, for example, ethanol, methanol, isopropanol, mixtures thereof, and the like. Suitable surfactants may include surfactants, such as, for example, compounds containing silicone. Suitable surfactants may contain silicon or silane moiety or mixtures thereof. Dimethicons may be also be used as a surfactant, such as, for example, PEG-10 dimethicone, PEG-12 Dimethicone, mixtures thereof, and the like.

The following are exemplary foam hand sanitizer formulations that may be used to generate the high quality foam shown and described herein. The below exemplary formulas are mixed with air to form foam.

Formula 1

Water; Caprylyl Glycol; 60 to 80% Alcohol Dent SDA 3C 190; Glycerin, 1 to 5% PEG-12 Dimethicone; Isopropyl Myristate; Tocopheryl Acetate, Niacinamide, Avenanthramide, PPG-12/SMDI Copolymer, EO Blend and LBM.

Formula 2

Water; 60-80% Alcohol: SDA 3-C, 190 Proof; 0 to 2% PEG-12 Dimethicone; 1 to 3% PEG-10 Dimethicone; Hydroxy Ethylurea; Glycerine USP; Propylene Glycol; Isopropyl Myristate and Tocopheryl Acetate.

Formula 3

Water, 60-80% SDA 3C Alcohol; 0-5% Isopropanol, Anhydrous; Oto 3% PEG-32, 0 to 5% CHG 20% solution; 20 to 5% PEG-10 Dimethicone JPE; Isopropyl Myristate and Tocopheryl Acetate.

Formula 4

Water; 60-70% Alcohol; 1.5 to 5% Peg 10 Dimethicone; Glycerin 99% Usp Kosher, Fragrance, Propylene Glycol Usp, Isopropyl Myristate, Tocopheryl Acetate.

Formula 5

Water; Caprylyl Glycol, 65-80% Alcohol SDA 3C 190, Hydroxyethyl Urea Glycerin; 0.5 to 5% PEG-12 Dimethicone; Isopropyl Myristate and Tocopheryl Acetate.

Formula 6

Water, Caprylyl Glycol, 15-65% SDA 3C Alcohol; Glycerin, 0 to 5% PEG-12 Dimethicone, Isopropyl Myristate, Tocopheryl Acetate.

Formula 7

Water, Caprylyl Glycol, 15-35% SDA 3C Alcohol; Glycerin, 0 to 5% PEG-12 Dimethicone, Isopropyl Myristate, Tocopheryl Acetate.

Formula 8

Water, Caprylyl Glycol, 25-35% SDA 3C Alcohol; Glycerin, 0 to 5% PEG-12 Dimethicone, Isopropyl Myristate, Tocopheryl Acetate.

Other compositions having alcohol in the range of 15 to 85%, water, and a surfactant are contemplated herein. Further, many foaming alcohol compositions may be used to generate the high quality foam disclosed and claimed herein. Exemplary formulations that may provide suitable results, may be found in, for example, compositions shown and described in: US Pat. Pub. 2007/0,148,101, titled Foamable Alcoholic Composition; U.S. Pat. No. 8,530,152 titled Foaming Alcohol Compositions with Selected Dimethicone Surfactants; U.S. Pat. No. 7,190,090 titled High Alcohol Content Gel-Like And Foaming Compositions Comprising An Alcohol And Fluorosurfactant; U.S. Pat. Pub. No. 2013/0,165,530 titled Foamable Alcoholic Compositions With Skin Benefits; U.S. Pat. No. 8,263,098 titled High Alcohol Content Foaming Compositions With Silicone-Based Surfactants; U.S. Pat. Pub. No. 2011/0,104,079 titled Foamable Alcoholic Composition; all of which are incorporated herein by reference in their entirety.

As a way of characterizing the quality of alcohol based sanitizer foams, optical imaging was used to measure the bubble sizes in the foam of alcohol based foam sanitizers.

The foam shown and described herein was produced using two conventional non-aerosol foam pumps and the novel non-aerosol foam pumps and foam generators disclosed herein.

Figure 15:
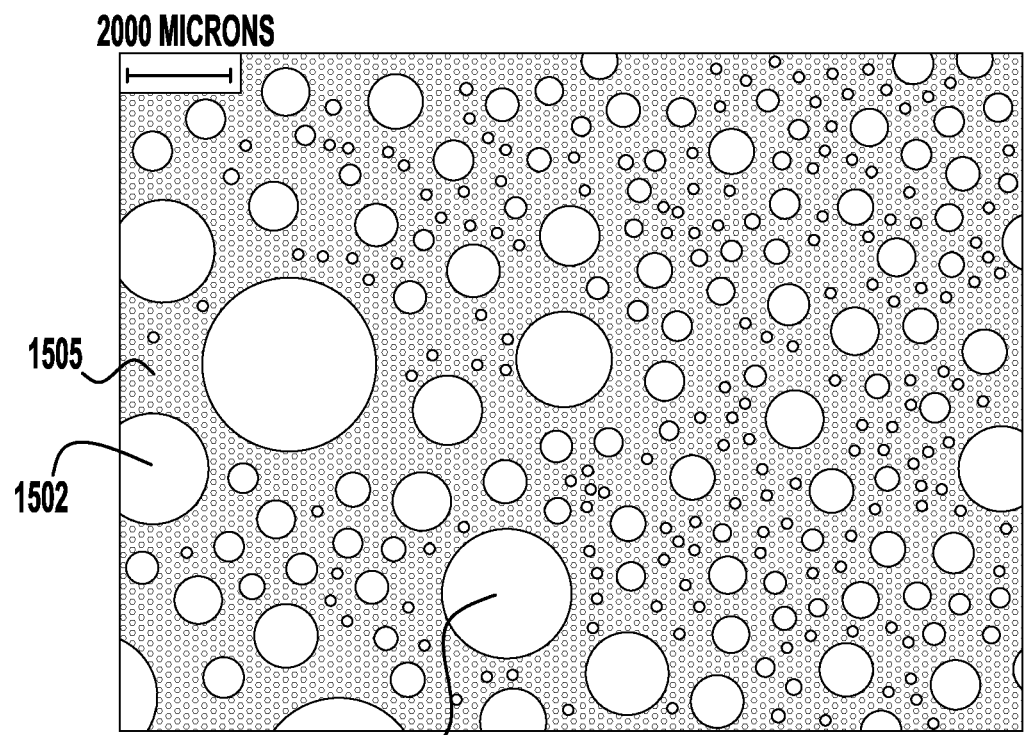
FIG. 15 is an image of an alcohol based foam foamed with a conventional pump manufactured by Albea under low lighting and low magnification.
Figure 16:
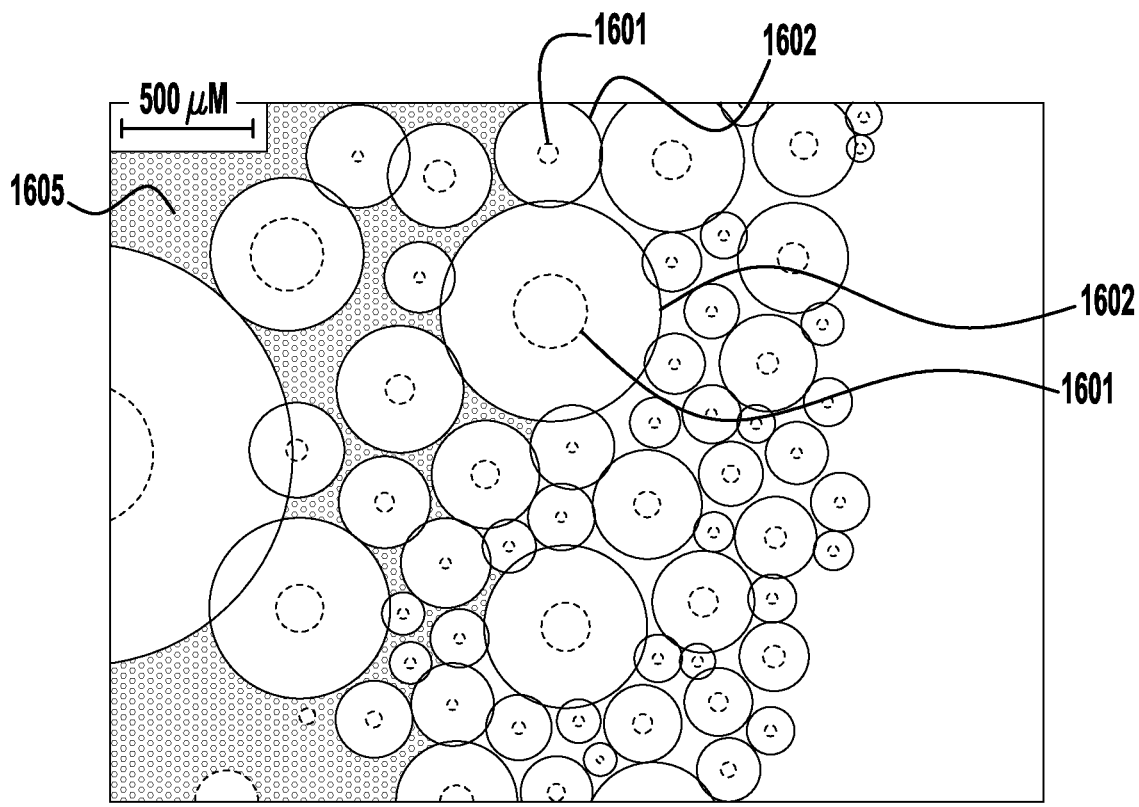
FIG. 16 is an image of an alcohol based foam foamed with a conventional pump manufactured by Albea under transmitted light at a higher magnification

The first pump was a conventional pump manufactured by Albea, model number F2-L11 which may be purchased at http://www.albea-group.com/en/products/product-catalog/f2.html. An exemplary embodiment of the Albea foam pump is shown and described in U.S. Pat. No. 6,053,364. This pump may be referred to herein as the "Air Spray" pump. FIG. 15 is an image of an alcohol based foam 1500 foamed with the conventional pump manufactured by Albea under low lighting and low magnification. Bubbles 1502 are visible under the low magnification in the denser foam mixture 1505 (the hatching of foam mixture 1505 indicates areas of foam where the bubbles were not individually identifiable). FIG. 16 is an image of an alcohol based foam 1500 foamed with the conventional pump manufactured by Albea under transmitted light at a higher magnification. The image was taken on the edge of the foam 1500, described in more detail below. As described below, the centers 1601 of the bubbles 1602 appeared light in the images and are denoted by the dashed lines. The bubbles 1602 are the same bubbles as bubbles 1502 but are denoted differently because they are under different magnifications. The foam mixture 1605 indicates areas of foam where the bubbles were not individually identifiable.

Figure 17:
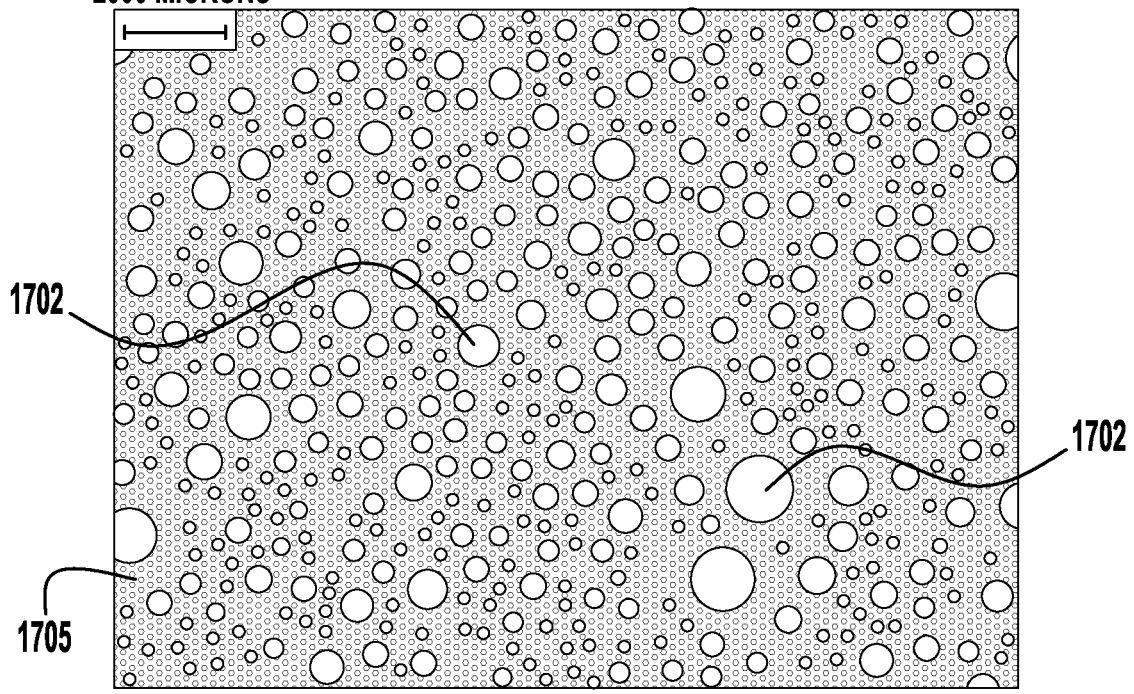
FIG. 17 is an image of an alcohol based foam foamed with a conventional pump manufactured by Ophardt under low lighting and low magnification.
Figure 18:
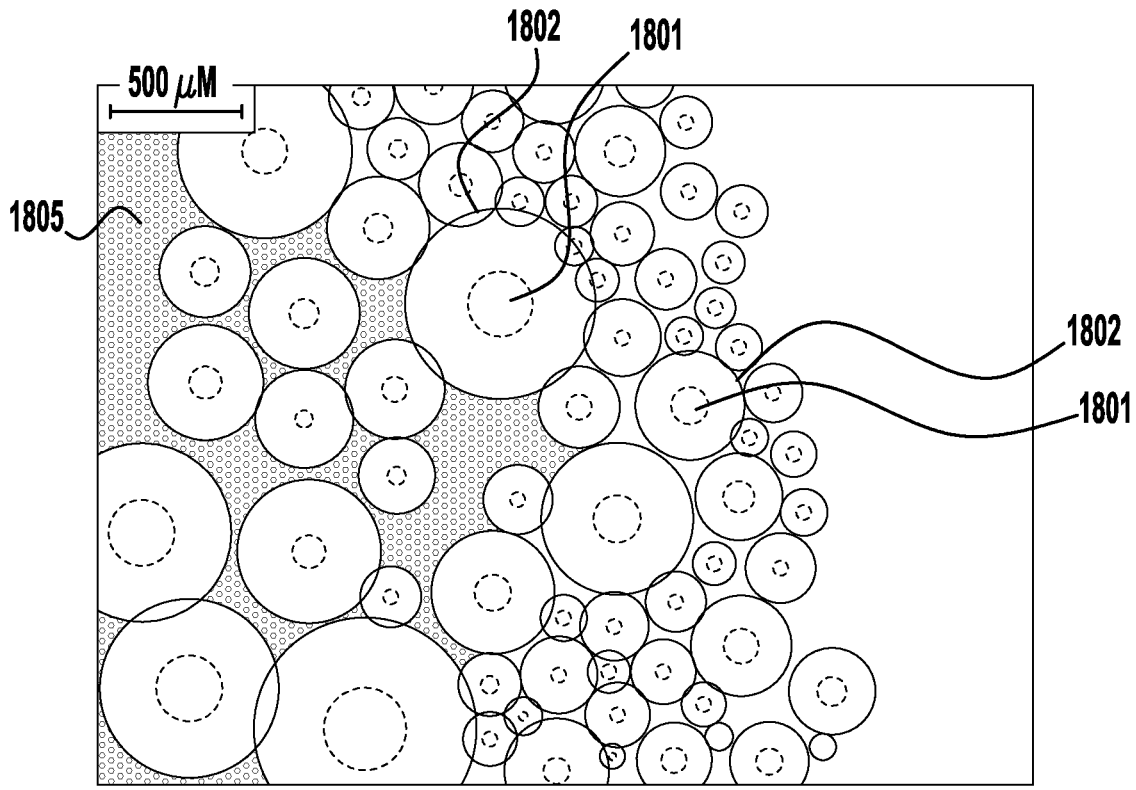
FIG. 18 is an image of an alcohol based foam foamed with a conventional pump manufactured by Ophardt under transmitted light at a higher magnification.

The second pump was a conventional pump manufactured by Ophardt, model number SD. An exemplary embodiment of the Ophardt foam pump is shown and described in U.S. Pat. Nos. 8,360,286 and 8,272,539. FIG. 17 is an image of an alcohol based foam 1700 foamed with the conventional pump manufactured by Ophardt under low lighting and low magnification. Bubbles 1702 are visible under the low magnification in the denser foam mixture 1705. The foam mixture 1705 indicates areas of foam where the bubbles were not individually identifiable. FIG. 18 is an image of an alcohol based foam 1700 foamed with the conventional pump manufactured by Ophardt under transmitted light at a higher magnification. The image was taken on the edge of the foam 1700, described in more detail below. As described below, the centers 1801 of the bubbles 1802 appeared light in the images and are denoted by the dashed lines. The bubbles 1802 are the same bubbles as bubbles 1702 but are denoted differently because they are under different magnifications. The foam mixture 1805 indicates areas of foam where the bubbles were not individually identifiable.

Figure 19:
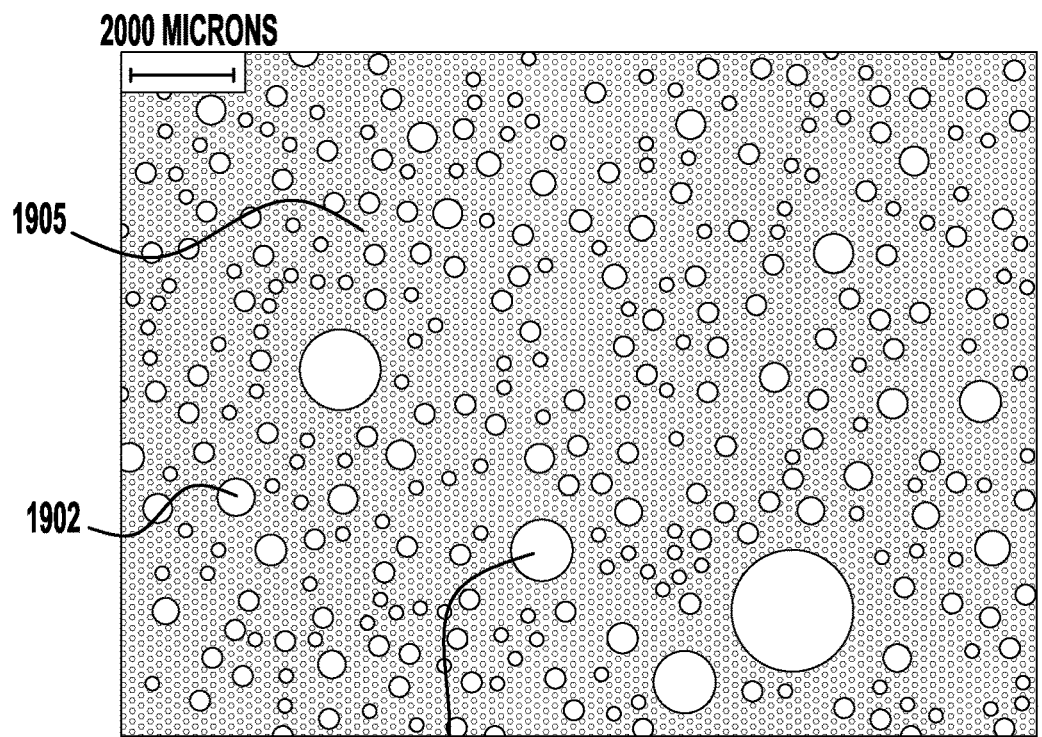
FIG. 19 is an image of an alcohol based foam foamed with novel sequentially operated diaphragm foam pumps shown and described herein under low lighting and low magnification.
Figure 20:
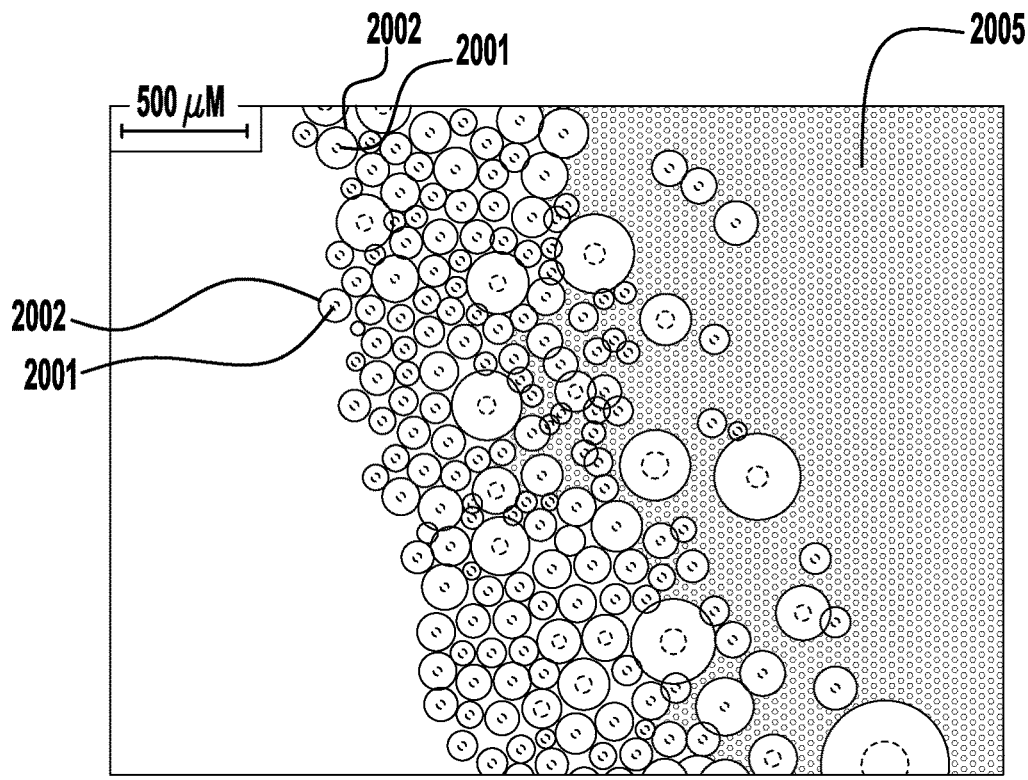
FIG. 20 is an image of an alcohol based foam foamed with novel sequentially operated diaphragm foam pumps shown and described herein under transmitted light at a higher magnification.

The third pump is the sequentially activated diaphragm foam pump described herein, which may be referred to as "wobble pump". FIG. 19 is an image of an alcohol based foam 1500 foamed with the wobble pump and the foam cartridge under low lighting and low magnification. Bubbles 1902 are visible under the low magnification in the denser foam mixture 1905. The foam mixture 1905 indicates areas of foam where the bubbles were not individually identifiable. FIG. 20 is an image of an alcohol based foam 1900 foamed with the wobble pump and the foam cartridge under transmitted light at a higher magnification. The image was taken on the edge of the foam 1900, described in more detail below. As described below, the centers 2001 of the bubbles 2002 appeared light in the images and are denoted by the dashed lines. The bubbles 2002 are the same bubbles as bubbles 1902 but are denoted differently because they are under different magnifications. The foam mixture 2005 indicates areas of foam where the bubbles were not individually identifiable.

To measure the foam bubble size, foam was floated on liquid, shaken slightly to disperse the foam and images were collected. The images were subsequently processed using standard image analysis techniques to identify and measure the bubble diameters. Due to the wide range of bubble sizes, two methods were developed to measure the bubble sizes; a low magnification method for measurement of large bubbles (diameters greater than 500 μm) and a higher magnification method to measure the smaller bubbles (diameters less than 500 μm).

For the low magnification images, the following amounts of foam were dispensed to have about the same volume of foam: Albea pump—2 pump strokes; Ophardt pump—50% of a pump stroke; sequentially activated diaphragm foam pump (wobble pump)—1 sec. The pumps were operated in a manner that resulted in the same volume of foam output. Half stroking the Ophardt pump did not make a difference in the foam quality. The petri dish was then gently shaken to disperse the foam on the liquid surface (without creating new bubbles). A clear glass cover placed on top of the dish, without contacting the bubbles, in order to reduce evaporation. The lower magnification images were collected with the Q-Color Digital Camera, C-mounted to Canon FD lens adaptor, a 50 mm Canon lens (F1.8, infinity focus), and a +10 macro lens filter, mounted on a focusing stand. The lower magnification images were calibrated with a mm-scale ruler.

As summarized in Table I, below the Albea pump (identified as Air Spray Pump) produced the largest bubbles (Shown in FIG. 15), followed by the sequentially activated diaphragm foam pump (shown in FIG. 19) and Ophardt pump (identified as the "SD Pump") (shown in FIG. 17). Although the sequentially activated diaphragm foam pump (identified as "Wobble Pump" in the Table) produced some bubbles that were larger than the Ophardt pump, there were fewer numbers of large bubbles in comparison to the overall total number of bubbles.

TABLE I

| Image # | Air Spray Pump | | | | SD Pump | | | | Wobble Pump | | | |
| --- | --- | --- | --- | --- | --- | --- | --- | --- | --- | --- | --- | --- |
|  | A | B | C | Total | A | B | C | Total | A | B | C | Total |
| Maximum Bubble Diameter (μm) | 3614 | 4284 | 3573 |  | 1385 | 1300 | 1637 |  | 2455 | 2935 | 2111 |  |
| # Bubbles with Diameters 1500-3000 μm | 1 | 1 | 3 | 5 | 0 | 0 | 1 | 1 | 2 | 1 | 2 | 5 |
| # Bubbles with Diameters >3000 μm | 3 | 1 | 1 | 5 | 0 | 0 | 0 | 0 | 0 | 0 | 0 | 0 |

For all images, the Q-Color Digital camera was controlled by Q Color Pro software (version 5.1.1.14) running on a personal computer with Windows XP operating system. All images were collected in 8-bit gray-scale mode and stored as TIFF files. Images were imported into Adobe Photoshop (version 7.0.1) and Fovea Pro plug-ins (version 4.0 by Reindeer Graphics) for analysis. Measurement results were exported to Microsoft Excel for statistical calculations. The low magnification images were processed by blurring the image using a Gaussian blur filter with a 15 pixel radius, thresholding the blurred images to select the dark areas, and the measuring the identified bubble sizes. Overhead room lighting was used to illuminate the samples, resulting in reflections from the overhead lights in the larger bubbles; therefore the circumscribed radius was measured and used to calculate the corresponding bubble diameter in order to avoid this interference.

For the higher magnification, images were collected with the Q-Color Digital Camera with a UTV0.5×C-3 adaptor, a BX51 compound microscope with a 5× objective with transmitted light. Images were calibrated with a scale micrometer.

Using the Q Color Pro software, the high magnification images were processed by thresholding the images to select the bright areas, eliminating the small areas of less than 120-140 pixels caused by reflections between bubbles, removing a 1 pixel wide band around the border of the image, and measuring the resulting areas. Since selecting the bright areas selected a center portion from each bubble as well as areas between bubbles, areas with a roundness value greater than 0.6-0.75 were identified as bubble centers. Bubble diameters were calculated as the diameter of the identified bubble center plus twice the minimum separation between the bubble center and closest bright area, which was expected to be the areas between bubbles. Also, since collecting images from the edges of the foam result in large areas of the image without bubbles, images were cropped to 1900×1200 or 1200×1900 pixels to examine consistent areas.

Average bubble diameters as well as size distribution charts from the high magnification method are shown below in Table II below. As can be seen from the chart, the measured bubble diameters produced by the sequentially activated diaphragm foam pump (identified as "Wobble Pump") (FIG. 20) were smaller than those produced by the Ophardt (FIG. 18) and Albea pumps (FIG. 16).

frequency of bubbles produced with the Ophardt pump (identified by "SD") had a diameter of between about 100 µm to 350 µm.

Figure 22:
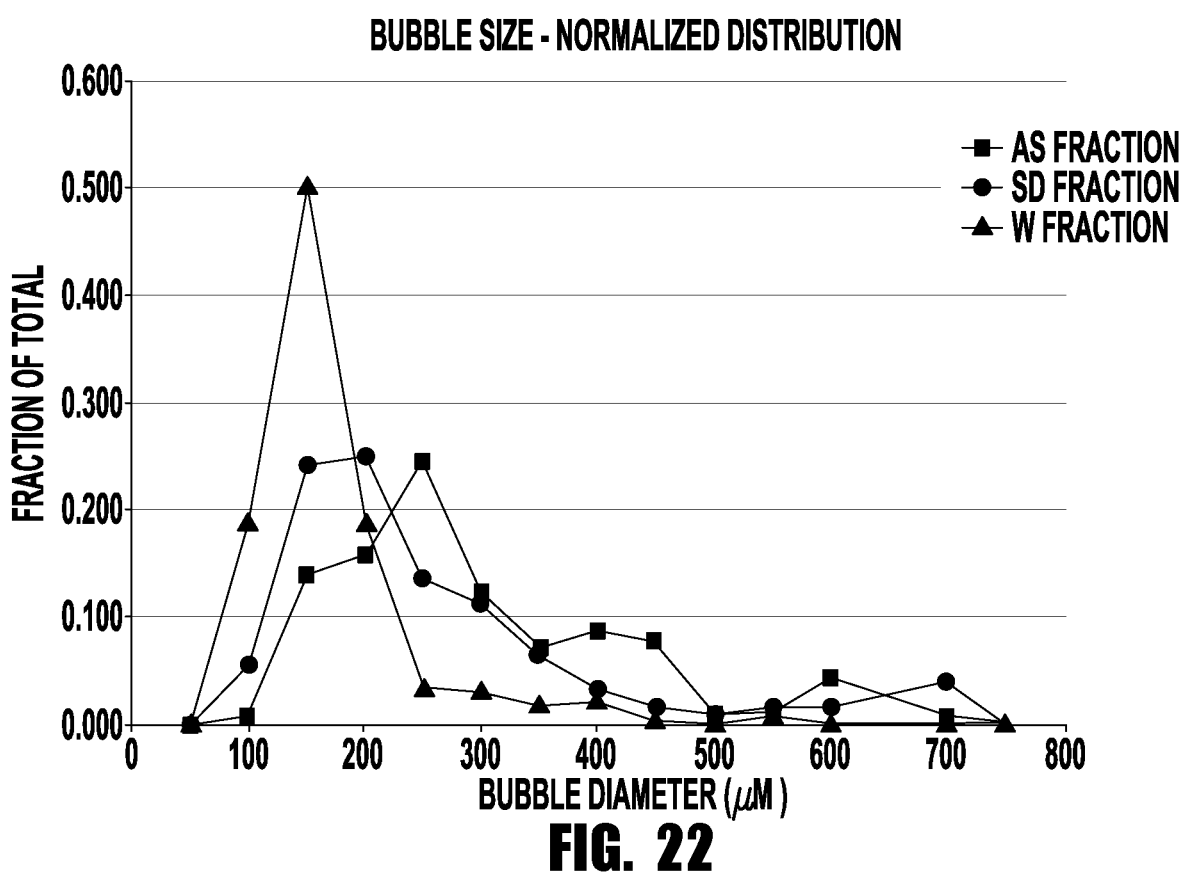
FIG. 22 is an graph that illustrates the frequency of the total bubble size distribution of the Albea pump, the Ophardt pump and the novel diaphragm foam pump disclosed herein.

FIG. 22 illustrates that the sequentially activated foam diaphragm pump (identified with a "W") produced foam bubbles that exhibit smaller bubble sizes and the majority of the bubbles were less than about 250 µm. In contrast, the Ophardt SD pump had a wider distribution of bubble sizes and a high percentage that were over 250 µm. Similar, the Albea AS pump had a wider distribution of bubble sizes and about half or more were over 250 µm.

It is believed that the high quantity of smaller bubbles provides a higher quality foam. It is also believed that the high number of small bubbles provides a better feel when rubbed on the skin. In addition it is believed that the smaller bubbles provide a more appealing visual image and a perception of a higher quality foam to a user. It further believed that the high quantity of small bubbles gives a user the perception of superior coverage. Other benefits of the inventive foam compared to the prior art foam may include consumers liking the inventive foam sanitizer better, feeling the inventive foam was not as runny or thin as the prior art foam, feeling the inventive foam was thick and more stationary than the prior art foam, feeling that there was less splashing off of their hands and less dripping on the floor with the inventive foam compared to the prior art foam and feeling that the inventive foam was more gentle on their skin than the prior art foam.

In addition to the bubble size, the foam density was measured. To measure the foam density, a graduated cylinder was used to capture the volume and a scale was used to capture the mass. The average foam density produced by the Albea pump was 0.090 g/ml, the Ophardt SD pump produced 0.095 g/ml, the sequentially activated diaphragm foam pump (or wobble pump) produced foam with a foam density of 0.109 g/ml. As can be seen, the sequentially activated diaphragm foam pump produced a higher density foam. The higher density foam has a better feel and a higher perceived quality.

Because the quality of the foam generated by Applicants is so much better than the foam generated by other non-aerosol foam pumps, Applicants also measured the bubble

TABLE II

| | Air Spray Pump | | | SD Pump | | | Wobble Pump | |
|---|---|---|---|---|---|---|---|---|
| Image # | A | B | C | A | B | C | A | C |
| Total Features | 107 | 117 | 72 | 142 | 61 | 129 | 265 | 357 |
| Round Features (Bubble Centers) | 37 | 44 | 33 | 67 | 17 | 40 | 89 | 138 |
| Minimum Diameter (µm) | 140 | 93 | 122 | 61 | 148 | 103 | 91 | 60 |
| Maximum Diameter (µm) | 801 | 583 | 993 | 620 | 836 | 661 | 540 | 379 |
| Average Diameter (µm) | 291 | 231 | 328 | 193 | 371 | 245 | 168 | 134 |
| Standard Deviation (µm) | 137 | 113 | 184 | 99 | 214 | 142 | 82 | 60 |
| Pooled Average Diameter (µm) | | 278 | | | 234 | | 147 | |

Figure 21:
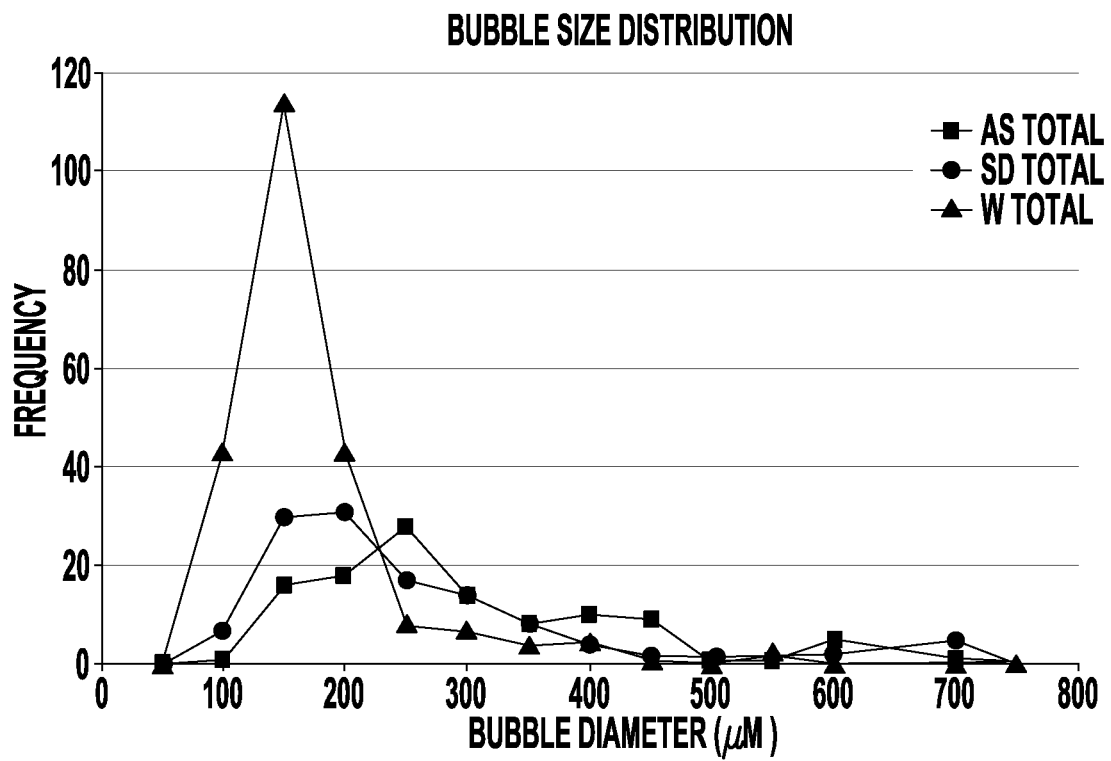
FIG. 21 is an graph that illustrates the bubble size distribution of the Albea pump, the Ophardt pump and the novel diaphragm foam pump disclosed herein.

Size distributions from the high magnification images are shown in FIGS. 21-22. FIG. 21 has the bubble size along the x-axis and the frequency of the bubble size along the y-axis. As can be seen in FIG. 21, a large portion of the frequency of bubbles produced with the sequentially activated foam pump (identified with a "W") had a diameter of between about 50 µm and about 250 µm. In contrast, a large portion of the frequency of bubbles produced with the Albea pump (identified by "AS") had a diameter of between about 150 µm and about 450 m and, similarly, a large portion of the characteristics of foam produced by an aerosol, using Ecolab's Quick Care Aerosol foam sanitizer to make a comparison of Applicants high quality non-aerosol foam with an aerosol foam. Foam generated by use of aerosol typically have small bubbles and provide a foam that is aesthetically pleasing and has a high quality feel.

To measure the bubble characteristics of an aerosol foam, a small amount of Purell liquid was carefully poured into a petri dish without forming bubbles. A small amount of aerosol foam (Ecolab Quick Care Aerosol Foam) was then dispensed onto the liquid Purell. The petri dish was gently shaken to disperse the foam slightly on the liquid surface (without creating new bubbles) and the optical images were collected. The images were collected with the Q-Color Digital Camera with a U-TV0.5×C-3 adaptor, a BX51 compound microscope with a 5× objective using transmitted light. Images were calibrated with a scale micrometer.

The Q-Color Digital camera was controlled by Q Color Pro software (version 5.1.1.14) running on a personal computer with Windows XP operating system. All images were collected in 8-bit gray-scale mode and stored as TIFF files. Images were imported into Adobe Photoshop (version 7.0.1) and Fovea Pro plug-ins (version 4.0 by Reindeer Graphics) for analysis. Measurement results were exported to Microsoft Excel for statistical calculations.

The images were processed by thresholding the images to select the bright areas, eliminating the small areas of less than 40 pixels caused by reflections between bubbles, removing a 1 pixel wide band around the border of the image, and measuring the resulting areas. Since selecting the bright areas selected a center portion from each bubble as well as areas between bubbles, areas with a roundness value greater than 0.75 were identified as bubble centers. Bubble diameters were calculated as the diameter of the identified bubble center plus twice the minimum separation between the bubble center and closest bright area, which was expected to be the areas between bubbles. Also, since collecting images from the edges of the foam result in large areas of the image without bubbles, images were cropped to 1900×1200 or 1200×1900 pixels to examine consistent areas.

The average bubble diameter for aerosol foam samples was between about 121-135 µm with an overall average diameter of 127 µm. These sizes were slightly smaller than the 147 µm average diameter observed for the sequentially operated diaphragm foam pump. However, the average diameter of the bubble for the sequentially operated diaphragm foam pump (147 µm) were much closer to the average diameter bubble size of the aerosol then the conventional non-aerosol foam pumps (278 µm) (234 µm). Accordingly, the novel embodiments of the sequentially operated foam pump disclosed herein provide a non-aerosol foam quality that compares with the foam quality of the aerosol without the need for hydrocarbon propellants. The novel foams claimed herein are formed using ambient air and are substantially free of hydrocarbons, do not require hydrocarbon based propellants and are more environmentally friendly.

While the present invention has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Moreover, elements described with one embodiment may be readily adapted for use with other embodiments. Therefore, the invention, in its broader aspects, is not limited to the specific details, the representative apparatus, and illustrative examples shown and described. Accordingly, departures may be made from such details without departing from the spirit or scope of the applicants' general inventive concept.

The invention claimed is:

1. A non-aerosol foam sanitizer product comprising:
   foam bubbles formed from a liquid mixture entrapping air;
   wherein the liquid mixture comprises between 40% and 85% by weight of a $C_1$-$C_8$ alcohol, at least one surfactant, and water;
   wherein air is entrapped in the liquid mixture by repeatedly pumping a shot of the liquid mixture through a liquid pumping mechanism into a mixing chamber followed by pumping two or more shots of ambient air through two or more air pumping mechanisms into the mixing chamber to mix with the liquid mixture to form the foam product that is comprised of a plurality of foam bubbles
   wherein at the time they are dispensed from a dispenser, more than about 50 percent of the foam bubbles have a diameter of between about 50 µm and about 250 µm.

2. The non-aerosol foam sanitizer product of claim 1 wherein the foam bubbles have a density of greater than about 0.10 grams/millimeter.

3. The non-aerosol foam sanitizer product of claim 1 wherein the surfactant comprises a compound containing silicone.

4. The non-aerosol foam sanitizer product of claim 1 wherein the surfactant comprises silane.

5. The non-aerosol foam sanitizer product of claim 1 wherein the surfactant comprises dimethicone.

6. The non-aerosol foam sanitizer product of claim 1 wherein the alcohol by volume greater than about 60%.

7. The non-aerosol foam sanitizer product comprising:
   a plurality of foam bubbles;
   wherein the plurality of foam bubbles are formed by a mixture of at least about 40% of a $C_1$-$C_8$ alcohol, water, a surfactant and entrapped ambient air sourced from the atmosphere;
   wherein the plurality of foam bubbles are formed by pumping the at least about 40% of a C1-C8 alcohol, water and surfactant from a first pump chamber into a mixing chamber; and wherein air is pumped from a second pump chamber into the mixing chamber to mix with the at least about 40% of a C1-C8 alcohol, water and surfactant, and air is pumped from a third pump chamber into the mixing chamber to mix with the at least about 40% of a C1-C8 alcohol, water, surfactant and air in the mixing chamber; and
   wherein when the non-aerosol foam sanitizer product is dispensed from a dispenser, the average diameter of the foam bubbles are less than about 190 µm.

8. The non-aerosol foam sanitizer product of claim 7 wherein the average diameter of the foam bubbles are between about 160 µm and 190 µm.

9. The non-aerosol foam sanitizer product of claim 7 wherein the average diameter of the foam bubbles is about 180 µm.

10. The non-aerosol foam sanitizer product of claim 7 wherein the foam bubbles have a density of greater than about 0.10 grams/millimeter.

11. The non-aerosol foam sanitizer product of claim 7 wherein the surfactant comprises a compound containing silicone.

12. The non-aerosol foam sanitizer product of claim 7 wherein the alcohol by volume greater than about 70%.

13. The non-aerosol foam sanitizer product of claim 7 wherein the alcohol by volume greater than about 60%.

14. A non-aerosol foam sanitizer product comprising:
   a plurality of foam bubbles formed by entrapping air in a liquid mixture;
   the liquid mixture comprises one or more $C_1$-$C_8$ alcohols in an amount of between 40% and 85% by weight, at least one surfactant, and water;

wherein air is entrapped in the liquid mixture by repeatedly pumping a shot of the liquid mixture through a non-piston liquid pumping mechanism into a mixing chamber followed by pumping two or more shots of ambient air through one or more non-piston pumping mechanisms into the mixing chamber to mix with the liquid mixture to form the foam product that is comprised of a plurality of foam bubbles wherein more than about 50 percent of the foam bubbles have a diameter of between about 50 µm and about 250 µm at the time the non-aerosol foam sanitizer product is dispensed from a dispenser.

15. The non-aerosol foam sanitizer product of claim 14 wherein the foam bubbles have a density of greater than about 0.10 grams/millimeter.

16. The non-aerosol foam sanitizer product of claim 14 wherein the surfactant comprises a compound containing silicone.

17. The non-aerosol foam sanitizer product of claim 14 wherein the surfactant comprises silane.

18. The non-aerosol foam sanitizer product of claim 14 wherein the surfactant comprises dimethicone.

19. The non-aerosol foam sanitizer product of claim 14 wherein the alcohol by volume greater than about 60%.

20. The non-aerosol foam sanitizer product of claim 14 wherein the alcohol by volume is about 70%.

\* \* \* \* \*